(12) United States Patent
Schultz

(10) Patent No.: US 10,940,291 B2
(45) Date of Patent: Mar. 9, 2021

(54) CATHETER WITH MULTI-FUNCTIONAL CONTROL HANDLE HAVING LINEAR MECHANISM

(71) Applicant: BIOSENSE WEBSTER, INC., Irvine, CA (US)

(72) Inventor: Jeffrey William Schultz, Chino, CA (US)

(73) Assignee: BIOSENSE WEBSTER, INC., Irvine, CA (US)

( * ) Notice: Subject to any disclaimer, the term of this patent is extended or adjusted under 35 U.S.C. 154(b) by 258 days.

(21) Appl. No.: 16/030,601

(22) Filed: Jul. 9, 2018

(65) Prior Publication Data

US 2018/0318552 A1 Nov. 8, 2018

Related U.S. Application Data

(63) Continuation of application No. 15/431,648, filed on Feb. 13, 2017, now Pat. No. 10,016,576, which is a
(Continued)

(51) Int. Cl.
*A61M 25/00* (2006.01)
*A61B 5/04* (2006.01)
(Continued)

(52) U.S. Cl.
CPC ........... *A61M 25/0147* (2013.01); *A61B 5/04* (2013.01); *A61B 5/042* (2013.01); *A61B 5/0422* (2013.01);
(Continued)

(58) Field of Classification Search
CPC ......... A61B 18/1492; A61B 2017/003; A61M 25/0147; A61M 25/0136; A61M 25/0105;
(Continued)

(56) References Cited

U.S. PATENT DOCUMENTS

RE34,502 E 1/1994 Webster, Jr.
5,987,344 A 11/1999 West
(Continued)

FOREIGN PATENT DOCUMENTS

EP 1457225 A2 9/2004
JP 02283347 A 11/1990
(Continued)

OTHER PUBLICATIONS

English translation of Chinese Office action dated Jul. 23, 2013 for Application No. 201010268804.1 (8 pages).
(Continued)

*Primary Examiner* — Joseph A Stoklosa
*Assistant Examiner* — Brian M Antiskay
(74) *Attorney, Agent, or Firm* — Lewis Roca Rothgerber Christie LLP

(57) ABSTRACT

A catheter for use in a patient's heart, especially for mapping a tubular region of the heart, has a catheter body, a deflectable intermediate section and a distal a mapping assembly that has a generally circular portion adapted to sit on or in a tubular region of the heart. A control handle of the catheter allows for single-handed manipulation of various control mechanisms that can deflect the intermediate section and contract the mapping assembly by means of a deflection control assembly and a linear control assembly. The deflection control assembly has a deflection arm and a rocker member. The linear control assembly has a linear control member, an inner rotational member and a cam. A pair of puller members are responsive to the deflection control assembly to bi-directionally deflect the intermediate section. A third puller member is responsive to the linear control assembly to contract the generally circular portion of the mapping assembly.

20 Claims, 24 Drawing Sheets

Related U.S. Application Data continuation of application No. 14/300,063, filed on Jun. 9, 2014, now Pat. No. 9,566,416, which is a continuation of application No. 12/550,204, filed on Aug. 28, 2009, now Pat. No. 8,747,351.

(51) Int. Cl.

| | | |
|---|---|---|
| *A61M 25/01* | (2006.01) | |
| *A61B 5/042* | (2006.01) | |
| *A61B 5/00* | (2006.01) | |
| *A61B 18/14* | (2006.01) | |
| *A61B 1/005* | (2006.01) | |
| *A61B 18/00* | (2006.01) | |

(52) U.S. Cl.
CPC ........ *A61B 5/6857* (2013.01); *A61B 18/1492* (2013.01); *A61M 25/0136* (2013.01); *A61B 1/0058* (2013.01); *A61B 2018/00351* (2013.01); *A61B 2018/00577* (2013.01); *A61M 2025/015* (2013.01); *A61M 2025/0161* (2013.01)

(58) Field of Classification Search
CPC .......... A61M 25/0133; A61M 25/0043; A61M 25/0113; A61M 2025/0063; A61M 25/01; A61M 25/09
USPC ..... 600/372, 374, 380, 466; 604/95.04, 528; 606/32, 41; 607/101–102, 119, 122
See application file for complete search history.

(56) References Cited

U.S. PATENT DOCUMENTS

| | | | |
|---|---|---|---|
| 6,066,125 | A | 5/2000 | Webster, Jr. |
| 6,123,699 | A | 9/2000 | Webster, Jr. |
| 6,171,277 | B1 | 1/2001 | Ponzi |
| 6,183,463 | B1 | 2/2001 | Webster, Jr. |
| 6,491,681 | B1 | 12/2002 | Kunis et al. |
| 6,500,167 | B1 | 12/2002 | Webster, Jr. |
| 6,741,878 | B2 | 5/2004 | Fuimaono et al. |
| 6,987,995 | B2 | 1/2006 | Drysen |
| 7,274,957 | B2 | 9/2007 | Drysen |
| 7,931,616 | B2 | 4/2011 | Selkee |
| 2005/0119721 | A1 | 6/2005 | Rabkin et al. |
| 2005/0277875 | A1 | 12/2005 | Selkee |
| 2005/0288656 | A1 | 12/2005 | Koerner et al. |
| 2006/0241366 | A1 | 10/2006 | Falwell et al. |
| 2007/0232858 | A1 | 10/2007 | Macnamara et al. |
| 2008/0009882 | A1 | 1/2008 | Drysen |
| 2008/0103520 | A1 | 5/2008 | Selkee |
| 2010/0069834 | A1 | 3/2010 | Schultz |
| 2010/0168827 | A1 | 7/2010 | Schultz |

FOREIGN PATENT DOCUMENTS

| | | |
|---|---|---|
| JP | 2006000649 A | 1/2006 |
| JP | 2006504473 A | 2/2006 |
| WO | 2004039273 A2 | 5/2004 |
| WO | 2007002713 A2 | 1/2007 |

OTHER PUBLICATIONS

Extended European Search Report dated Nov. 7, 2012 for European Application No. 12187045.5 (7 pages).

Extended European Search Report dated Oct. 24, 2011 for European Application No. 10251525.1 (3 pages).

Japanese Patent Office action dated Feb. 28, 2014 for JP Application No. 2010-190478 (English translation) (4 pages).

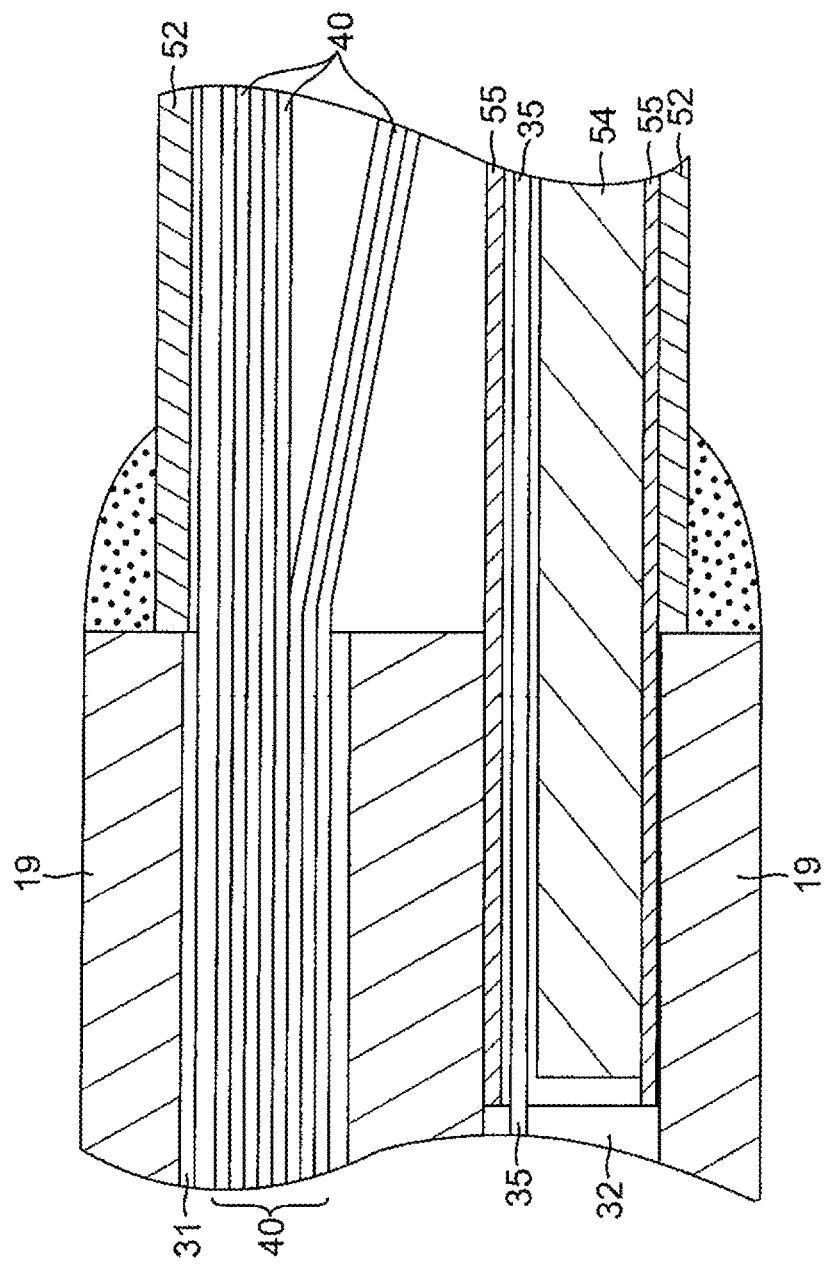

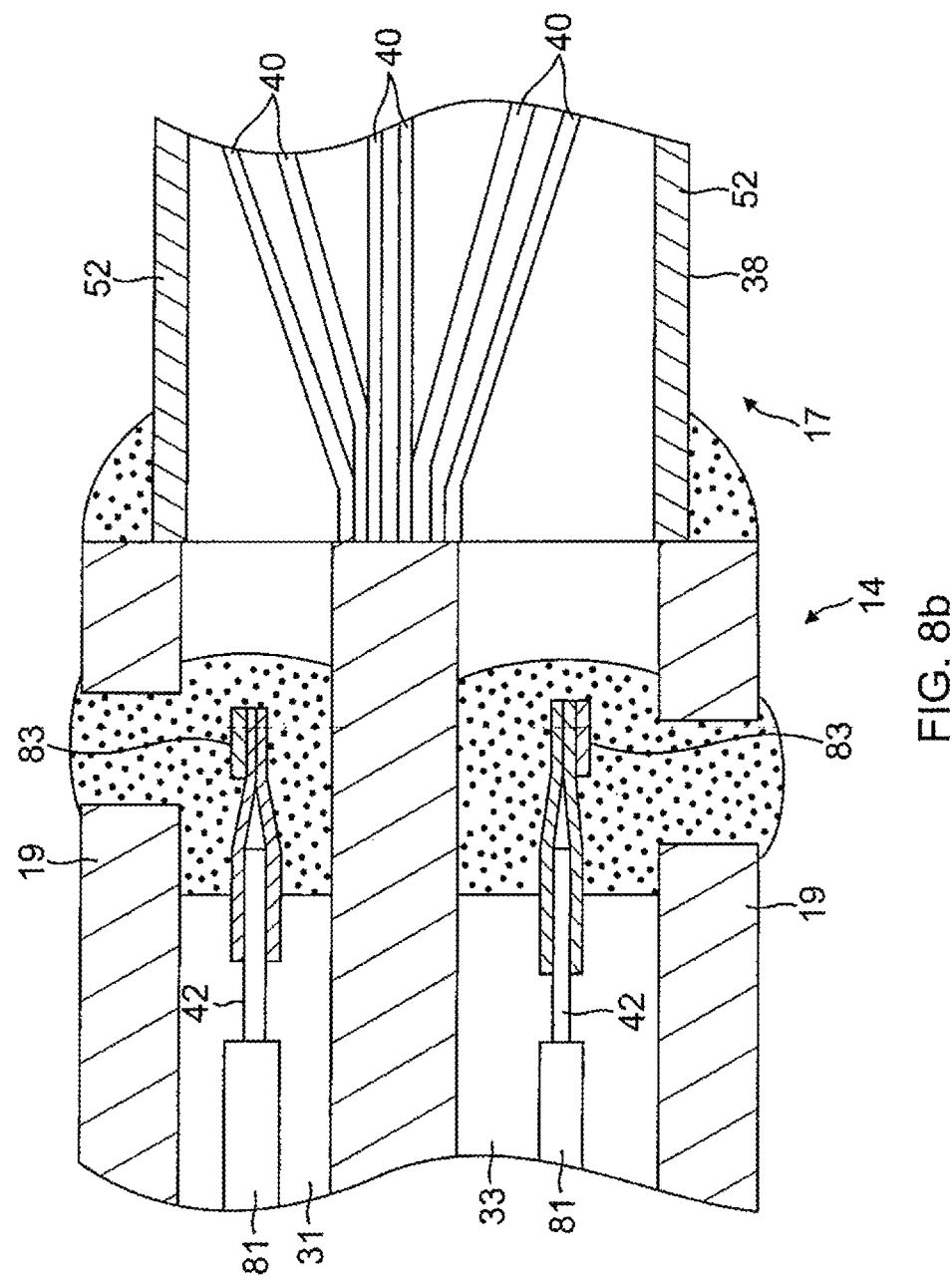

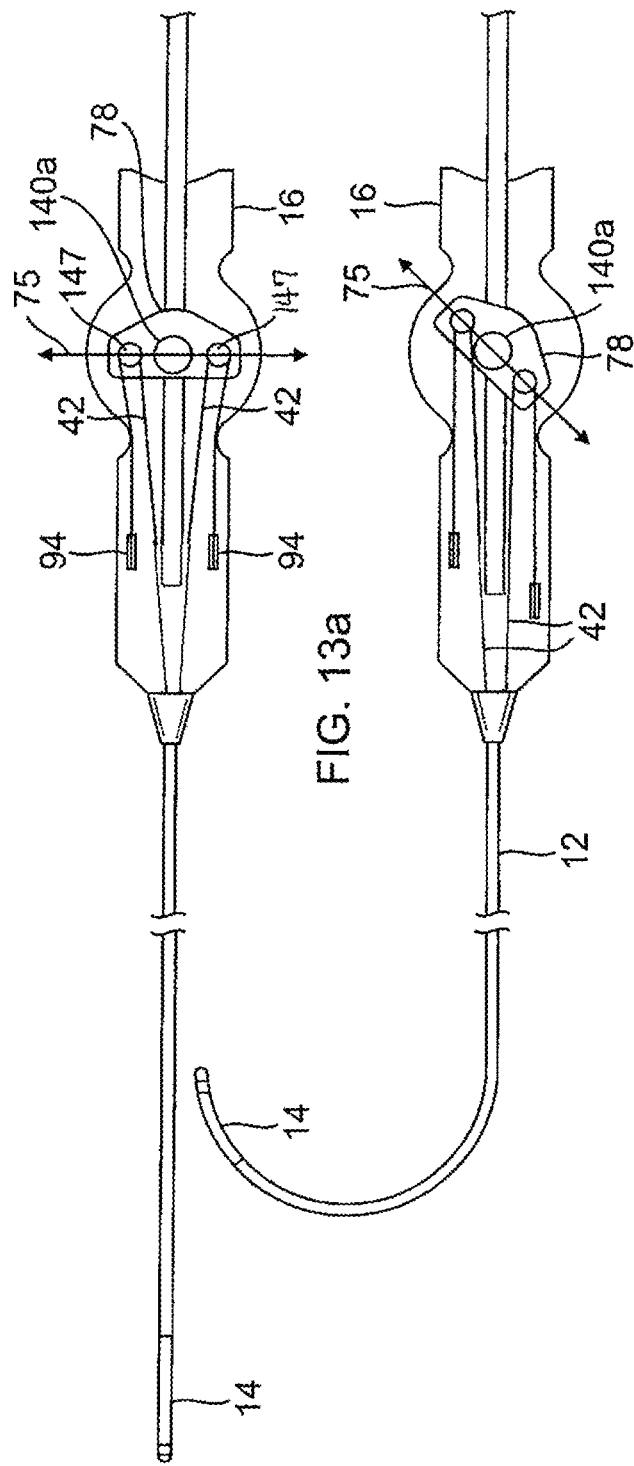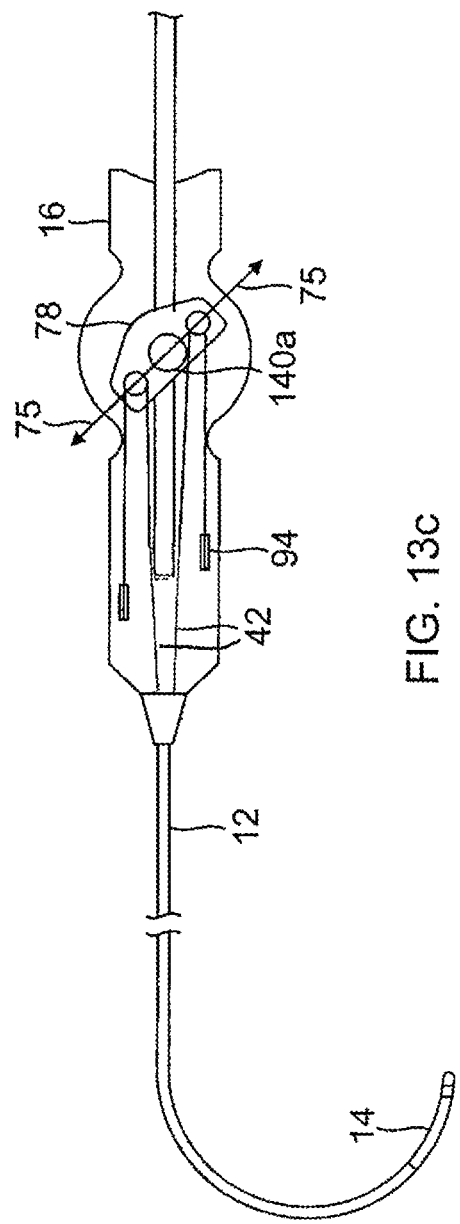
FIG. 13a
FIG. 13b
FIG. 13c

CATHETER WITH MULTI-FUNCTIONAL CONTROL HANDLE HAVING LINEAR MECHANISM

CROSS-REFERENCE TO RELATED APPLICATION

This application is a continuation of and claims priority to and the benefit of U.S. application Ser. No. 15/431,648 filed Feb. 13, 2017, now U.S. patent Ser. No. 10/016,576, which is a continuation of and claims priority to and the benefit of U.S. application Ser. No. 14/300,063, filed Jun. 9, 2014, now U.S. Pat. No. 9,566,416, which is a continuation of and claims priority to and the benefit of U.S. application Ser. No. 12/550,204 filed Aug. 28, 2009, now U.S. Pat. No. 8,747,351, the entire contents of all of which are incorporated herein by reference.

FIELD OF INVENTION

This invention relates to a catheter, in particular, a catheter with a control handle having multiple control mechanisms for deflecting and contracting portions of the catheter.

BACKGROUND

Electrode catheters have been in common use in medical practice for many years. They are used to stimulate and map electrical activity in the heart and to ablate sites of aberrant electrical activity. Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. Prior to treating the condition, one has to first determine the location of the wavelets. Various techniques have been proposed for making such a determination, including the use of catheters with a mapping assembly that is adapted to measure activity within a pulmonary vein, coronary sinus or other tubular structure about the inner circumference of the structure. One such mapping assembly has a tubular structure comprising a generally circular main region generally transverse and distal to the catheter body and having an outer circumference and a generally straight distal region distal to the main region. The tubular structure comprises a non-conductive cover over at least the main region of the mapping assembly. A support member having shape-memory is disposed within at least the main region of the mapping assembly. A plurality of electrode pairs, each comprising two ring electrodes, are carried by the generally circular main region of the mapping assembly.

In use, the electrode catheter is inserted into a guiding sheath which has been positioned a major vein or artery, e.g., femoral artery, and guided into a chamber of the heart. Within the chamber, the catheter is extended past a distal end of the guiding sheath to expose the mapping assembly. The catheter is maneuvered through movements that include deflection of a distal portion of the catheter so that the mapping assembly is positioned at the tubular region in the heart chamber. The ability to control the exact position and orientation of the catheter and also the configuration of the mapping assembly is critical and largely determines how useful the catheter is.

Steerable catheters are generally well-known. For example, U.S. Pat. No. Re 34,502 describes a catheter having a control handle comprising a housing having a piston chamber at its distal end. A piston is mounted in the piston chamber and is afforded lengthwise movement. The proximal end of the elongated catheter body is attached to the piston. A puller wire is attached to the housing and extends through the piston, through the catheter body, and into a tip section at the distal end of the catheter body. The distal end of the puller wire is anchored in the tip section of the catheter. In this arrangement, lengthwise movement of the piston relative to the housing results in deflection of the catheter tip section.

The design described in U.S. Pat. No. RE 34,502 is generally limited to a catheter having a single puller wire. If bi-directional deflection is desire, more than one puller wire becomes necessary. Moreover, if more control is desired, such as contraction of the mapping assembly, an additional puller wire is needed. Space is limited within a control handle and operation of puller wire control mechanisms must not interfere with components that extend through the control handle, such as lead wires, cables, and irrigation tubing. Moreover, it is desirable that the control mechanisms be arranged such that the catheter can be operated single-handedly by the user. Accordingly, a need exists for a control handle capable of moving three puller wires for at least two independent movements, such as bi-directional deflection of the catheter shaft and contraction of the mapping assembly, preferably through a single-handed manipulation of the user.

SUMMARY OF THE INVENTION

The present invention is directed to a catheter for use in a patient's heart, especially for mapping a tubular region of the heart. In one embodiment, the catheter has a catheter body and a deflectable intermediate section distal the catheter body. Distal the intermediate section is a mapping assembly that has a generally circular portion adapted to sit on or in a tubular region of the heart. A control handle of the catheter allows for single-handed manipulation of various control mechanisms that can deflect the intermediate section and contract the mapping assembly by means of a deflection control assembly and a linear control assembly. The deflection control assembly has a deflection arm and a rocker member. The linear control assembly has a linear control member, an inner rotational member and a cam. A pair of puller members are responsive to the deflection control assembly to bi-directionally deflect the intermediate section. A third puller member is responsive to the linear control assembly to contract the generally circular portion of the mapping assembly.

In a more detailed embodiment, a proximal end of the third puller member is anchored in the linear control assembly, such that actuation of the linear control member by a user moves the third puller member longitudinally relative to the catheter body. The linear control member has a portion that slidably engages housing of the control handle, and a projection that is received in a track formed on the inner rotational member such that distal and proximal movement of the control member along the longitudinal axis of the control handle rotates the inner rotational member to expand or retract the mapping assembly. Situated between the inner rotational member and the cam, a follower to which a proximal end of the third puller member is anchored is guided by a slot formed in the inner rotational member so as to slide in a cam track formed on the cam. Both the cam track and the track formed on the inner rotational member are helical to maximize efficiency of the linear control assembly in occupying a relatively small space in the control handle to achieve the linear motion desirable for expanding and contracting mapping assembly.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 8a is a side cross-sectional view of an embodiment of a junction between the intermediate section and the mapping assembly, taken along a first diameter.

FIG. 8b is a side cross-sectional view of an embodiment of a junction between the intermediate section and the mapping assembly, taken along a second diameter generally perpendicular to the first diameter.

FIGS. 13a-13c are schematics of an embodiment of the deflection control assembly in neutral and rotated configurations.

DETAILED DESCRIPTION OF THE INVENTION

Figure 1:
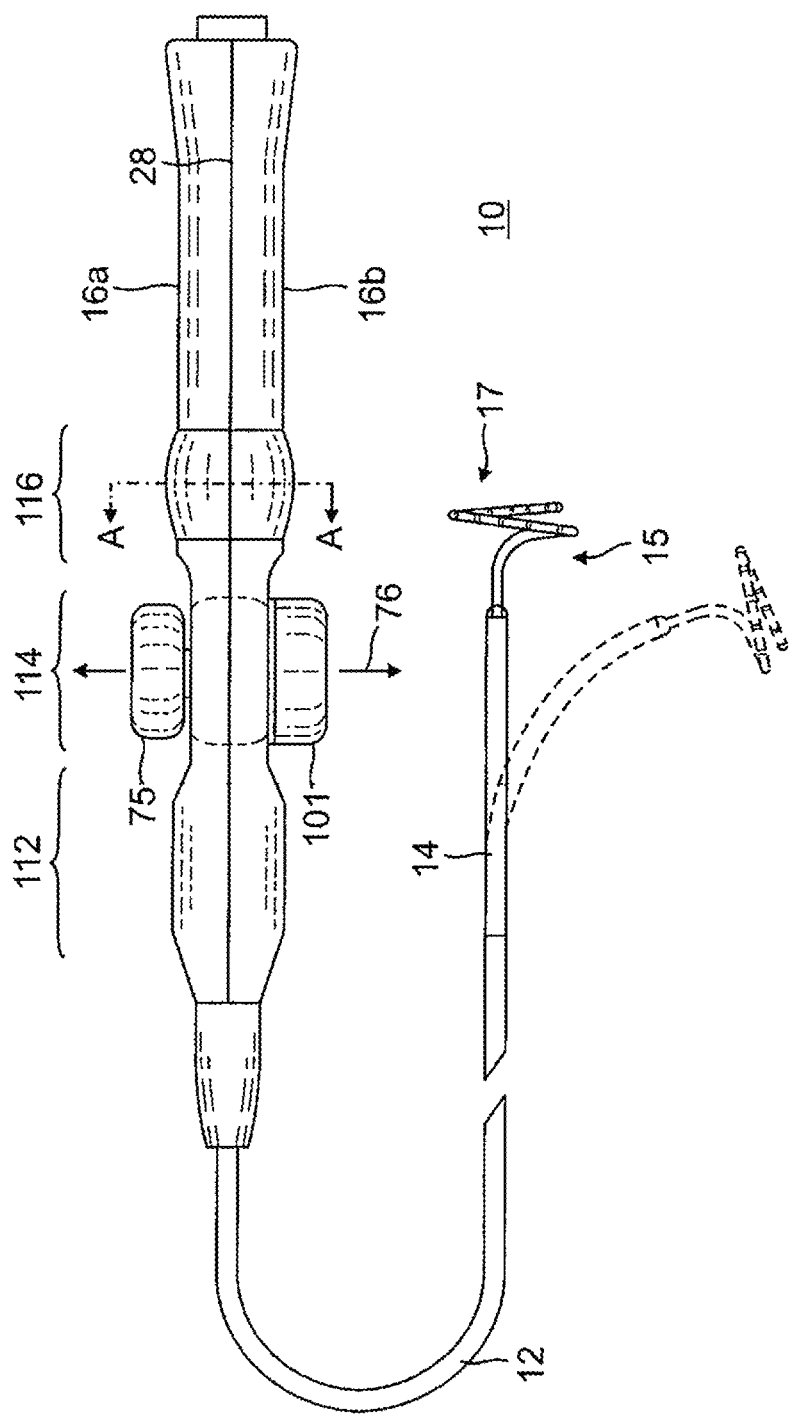
FIG. 1 is a top plan view of one embodiment of the catheter of the present invention.

Referring to FIG. 1, the present invention is directed to a catheter 10 with multiple control capabilities for mapping and/or ablation of the heart. In the illustrated embodiment of FIG. 1, a catheter 10 comprises an elongated catheter body 12, a deflectable intermediate section 14 at a distal end of the catheter body 12, a tip section 15 including a mapping assembly 17 at a distal end of the intermediate section 14, and a multi-functional control handle 16 at a proximal end of the catheter body 12 for controlling portions of the catheter, for example, deflecting the intermediate section 14 and contracting the mapping assembly 17.

Figure 2A:
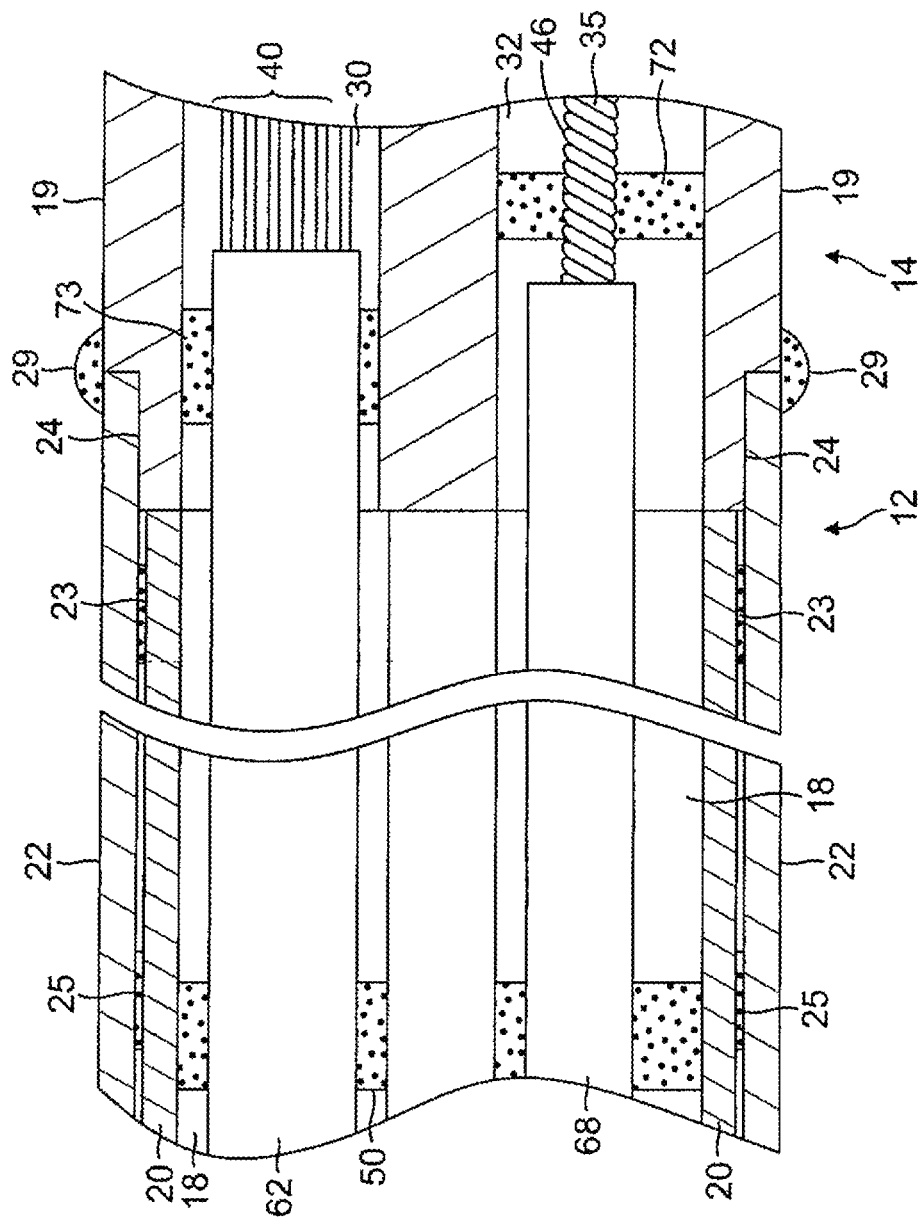
FIG. 2a is a side cross-sectional view of an embodiment of a junction of a catheter body and an intermediate section, taken along a first diameter.
Figure 2B:
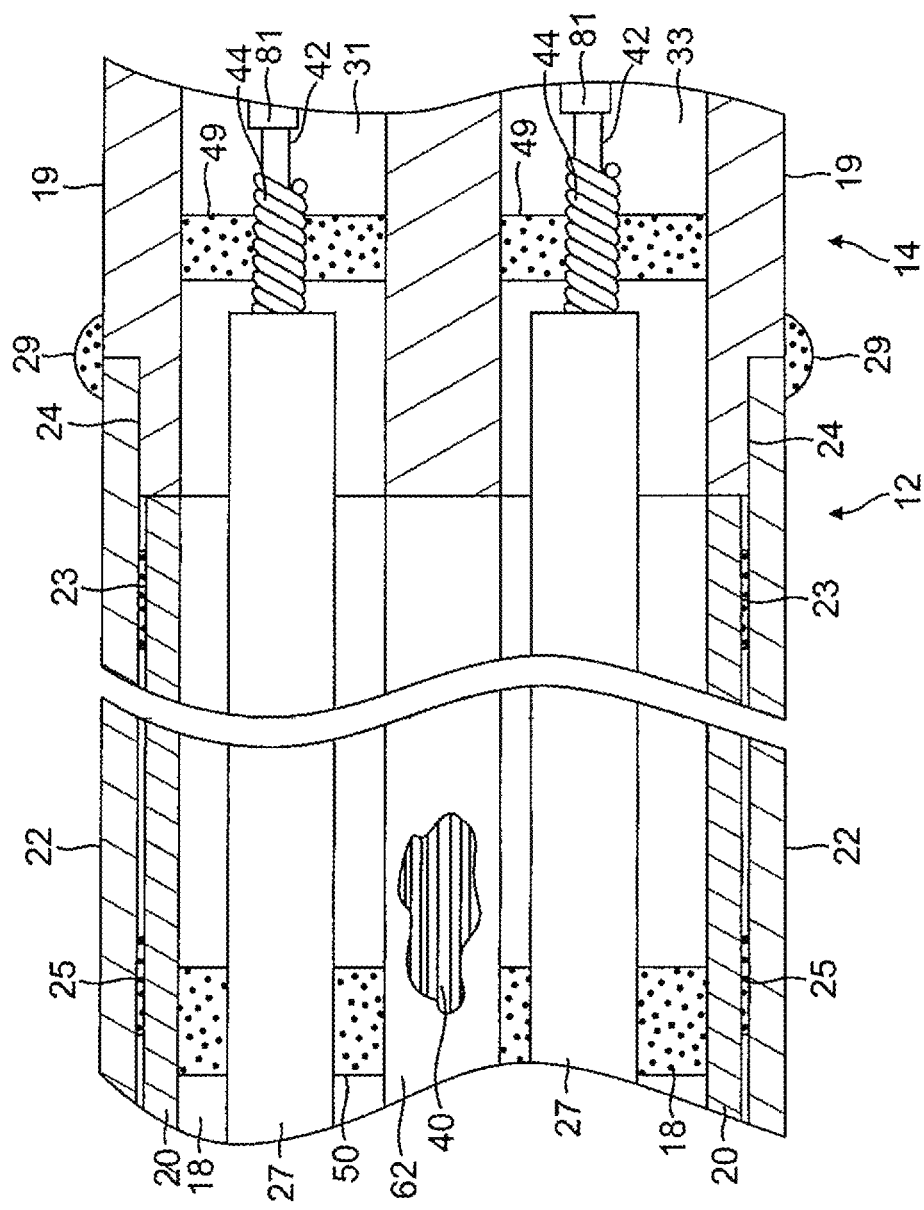
FIG. 2b is a side cross-sectional view of the embodiment of the junction of FIG. 2a, taken along a second diameter generally perpendicular to the first diameter.

With reference to FIGS. 2a and 2b, the catheter body 12 comprises a single, central or axial lumen 18. The catheter body 12 is flexible, i.e., bendable, but substantially non-compressible along its length. The catheter body 12 may be of any suitable construction and made of any suitable material. In one embodiment, the catheter body 12 comprises an outer wall 22 made of a polyurethane or nylon. The outer wall 22 comprises an imbedded braided mesh of stainless steel or the like to increase torsional stiffness of the catheter body 12 so that, when the control handle 16 is rotated, the tip section of the catheter 10 will rotate in a corresponding manner.

The outer diameter of the catheter body 12 is not critical, but is preferably no more than about 8 French. Likewise the thickness of the outer wall 22 is not critical. The inner surface of the outer wall 22 is lined with a stiffening tube 20, which can be made of any suitable material, preferably polyimide. The stiffening tube 20 is held in place relative to the outer wall 22 at the proximal end of the catheter body 12. A first glue joint 23 is made between the distal ends of the stiffening tube 20 and the outer wall 22 by a fast drying glue, e.g. Super Glue®. Thereafter a second glue joint 25 is formed between the proximal ends of the stiffening tube 20 and outer wall 22 using a slower drying but stronger glue, e.g., polyurethane.

The stiffening tube, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing is suitable because it may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, nylon or other similar material, particularly having a stainless steel braided mesh, the tendency for the polyimide stiffening tube 20 to kink when bent is essentially eliminated with respect to the applications for which the catheter is used.

In one embodiment, the outer wall 22 has an outer diameter of about 0.092 inch and an inner diameter of about 0.063 inch and the polyimide stiffening tube 20 has an outer diameter of about 0.0615 inch and an inner diameter of about 0.052 inch.

Figure 4:
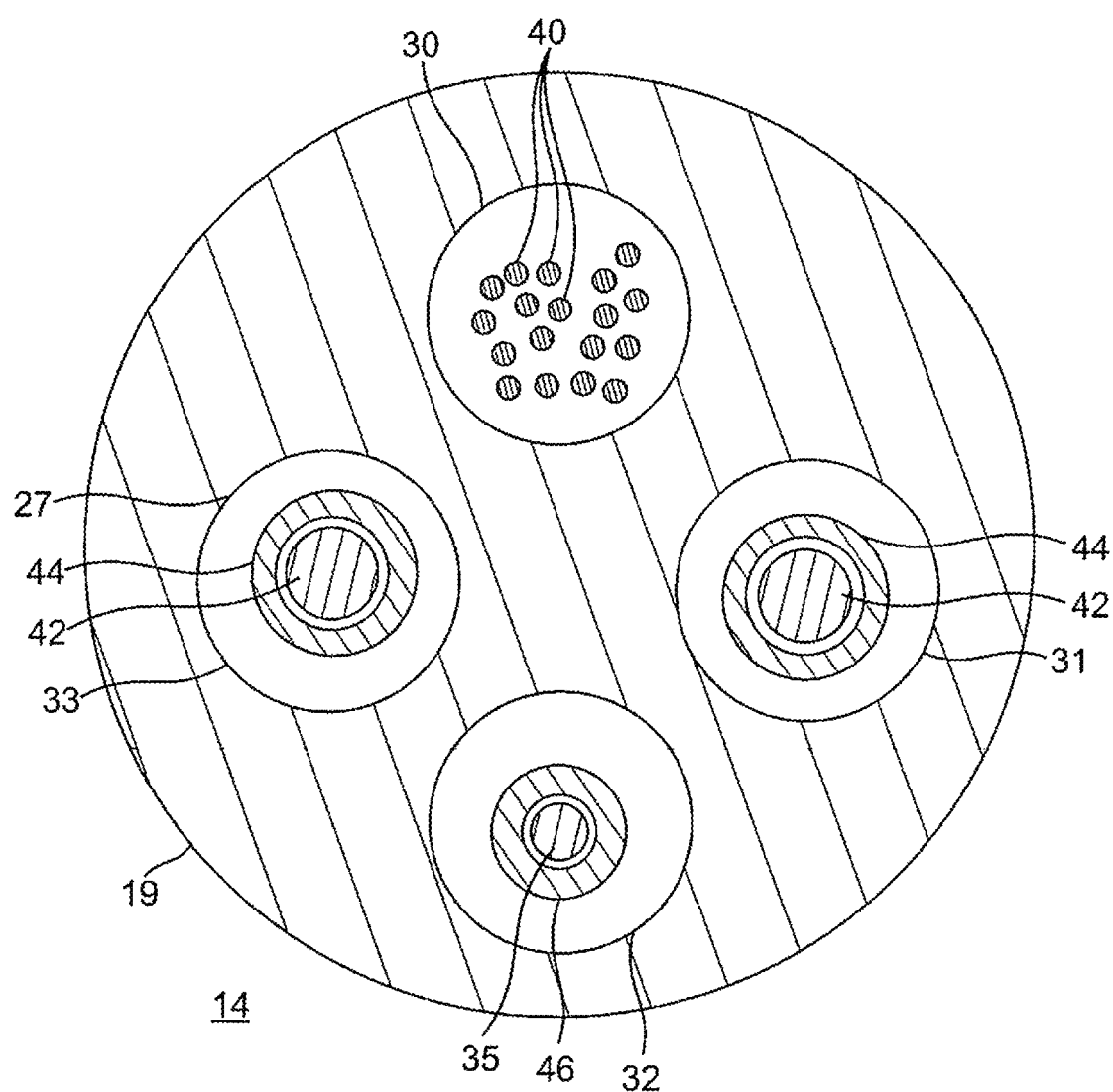
FIG. 4 is a longitudinal cross-sectional view of the intermediate section of FIG. 3, taken along line 4-4.

As shown in FIGS. 2a, 2b and 4, the intermediate section 14 comprises a shorter section of tubing 19 with multiple off-axis lumens, for example, first, second, third and fourth lumens 30, 31, 32 and 33. The tubing 19 is made of a suitable non-toxic material which is preferably more flexible than the catheter body 12. A suitable material for the tubing 19 is braided polyurethane, i.e., polyurethane with an embedded mesh of braided stainless steel or the like. The outer diameter of the intermediate section 14, like that of the catheter body 12, is preferably no greater than about 8 French. The size of the lumens is not critical. In one embodiment, the intermediate section has an outer diameter of about 7 French (0.092 inch) and the lumens are generally about the same size, having a diameter of about 0.022 inch, or selected lumens can have a slightly larger diameter of about 0.036 inch.

A means for attaching the catheter body 12 to the intermediate section 14 is illustrated in FIGS. 2a and 2b. The proximal end of the intermediate section 14 comprises an inner counter bore 24 that receives the outer surface of the polyimide stiffener 20. The intermediate section 14 and catheter body 12 are attached by glue 29 or the like.

As shown in FIGS. 2a and 2b, extending through the single lumen 18 of the catheter body 12 are various components, for example, lead wires and multiple puller members, and any other wires or cables. Longitudinal movement of the puller members relative to the catheter body 12 enable user control of various parts of the catheter via the control handle. In one embodiment, the puller members include a pair of deflection puller members 42 for deflecting the intermediate section 14 and a contraction puller member 35 for adjusting the mapping assembly 17 of the tip section 15.

A single lumen catheter body 12 may be preferred over a multi-lumen body because the single lumen 18 body can permit better tip control when rotating the catheter 10. The single lumen 18 permits the components passing therethrough to float freely within the catheter body. If such components were restricted within multiple lumens, they can build up energy when the handle 16 is rotated, resulting in the catheter body 12 having a tendency to rotate back if, for example, the handle is released, or if bent around a curve, to flip over, either for which are undesirable performance characteristics.

A deflection puller member 42 extends through the central lumen 18 of the catheter body 12 and into the second lumen 31 of the intermediate section 14. Another deflection puller member 42 extends through the central lumen 18 and into the fourth lumen 33 of the intermediate section 14. The distal ends of the deflection puller members 42 are anchored to the wall of the tubing 19 near the distal end of the intermediate section 14 by means of T-anchors 83 (FIG. 8B). In the intermediate section 14, each deflection puller members 42 extends through a plastic, e.g. Teflon®, sheath 81, which prevents the deflection puller members 42 from cutting into the wall of the tubing 19 of the intermediate section 14 when the intermediate section 14 is deflected.

As shown in FIG. 2b, compression coils 44 in surrounding relation to the deflection puller members 42 extend from the proximal end of the catheter body 12 to the proximal end of the intermediate section 14. The compression coils 44 are made of any suitable metal, e.g., stainless steel. The compression coils 44 are tightly wound on itself to provide flexibility, i.e., bending, but to resist compression. The inner diameter of the compression coils 44 is preferably slightly larger than the diameter of the puller wires 42. For example, when a puller member 42 has a diameter of about 0.007 inches, the compression coil 44 preferably has an inner diameter of about 0.008 inches. The Teflon® coating on the puller member 42 allows them to slide freely within the compression coils 44. The outer surface of the compression coils 44 is covered by a flexible, non-conductive sheath 27 to prevent contact between the compression coils 44 and other components, such as lead wires and cables, etc. In one embodiment, a non-conductive sheath is made of polyimide tubing.

The compression coils 44 are anchored at their proximal ends to the proximal end of the stiffening tube 20 in the catheter body 12 by glue joint 50 (FIG. 2b) and at its distal end near the proximal end of the intermediate section 14 in the second lumen 31 and fourth lumen 33 by glue joints 49 (FIG. 2b).

Figure 3:
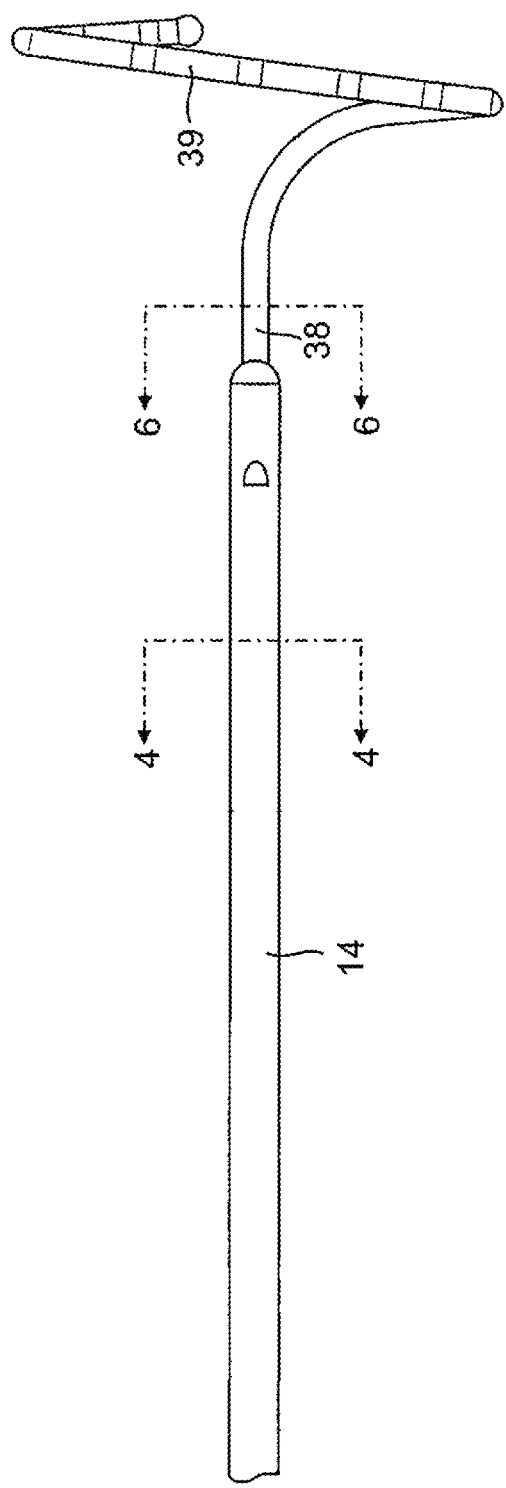
FIG. 3 is a side view of a distal portion of the catheter of FIG. 1, including an intermediate section and a mapping assembly.

With reference to FIG. 3, at the distal end of the intermediate section 14 is the mapping assembly 17. The mapping assembly 17 comprises a generally straight proximal region 38 and a generally circular main region 39. The proximal region 38 is mounted on the intermediate section 14, as described in more detail below, so that its axis can be a linear axial extension of the intermediate section 14. The proximal region 38 has an exposed length, e.g., not contained within the intermediate section 14, ranging from about 3 mm to about 12 mm, more preferably about 3 mm to about 8 mm, still more preferably about 5 mm, but can vary as desired.

Figure 5:
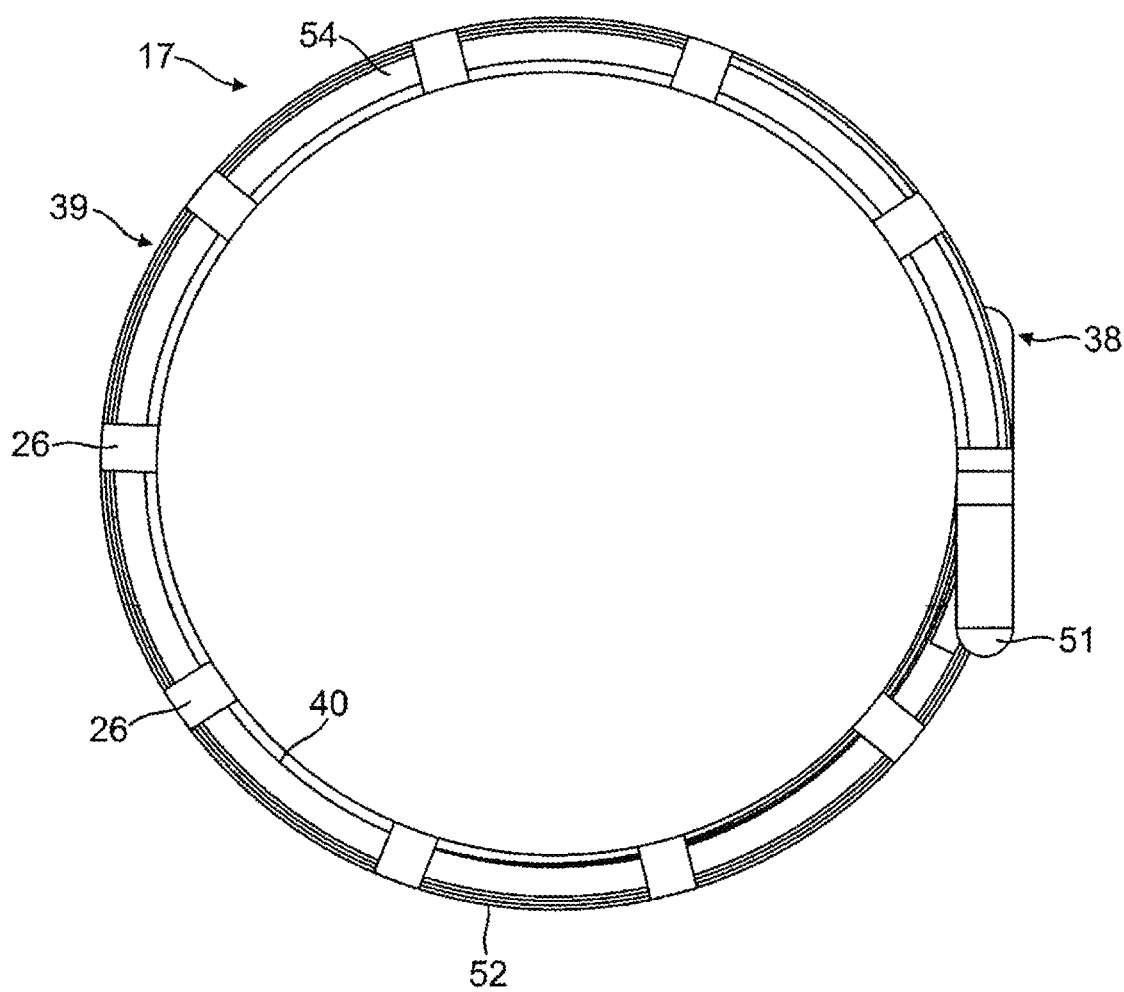
FIG. 5 is a schematic view of the mapping assembly showing one arrangement of the ring electrodes.
Figure 6:
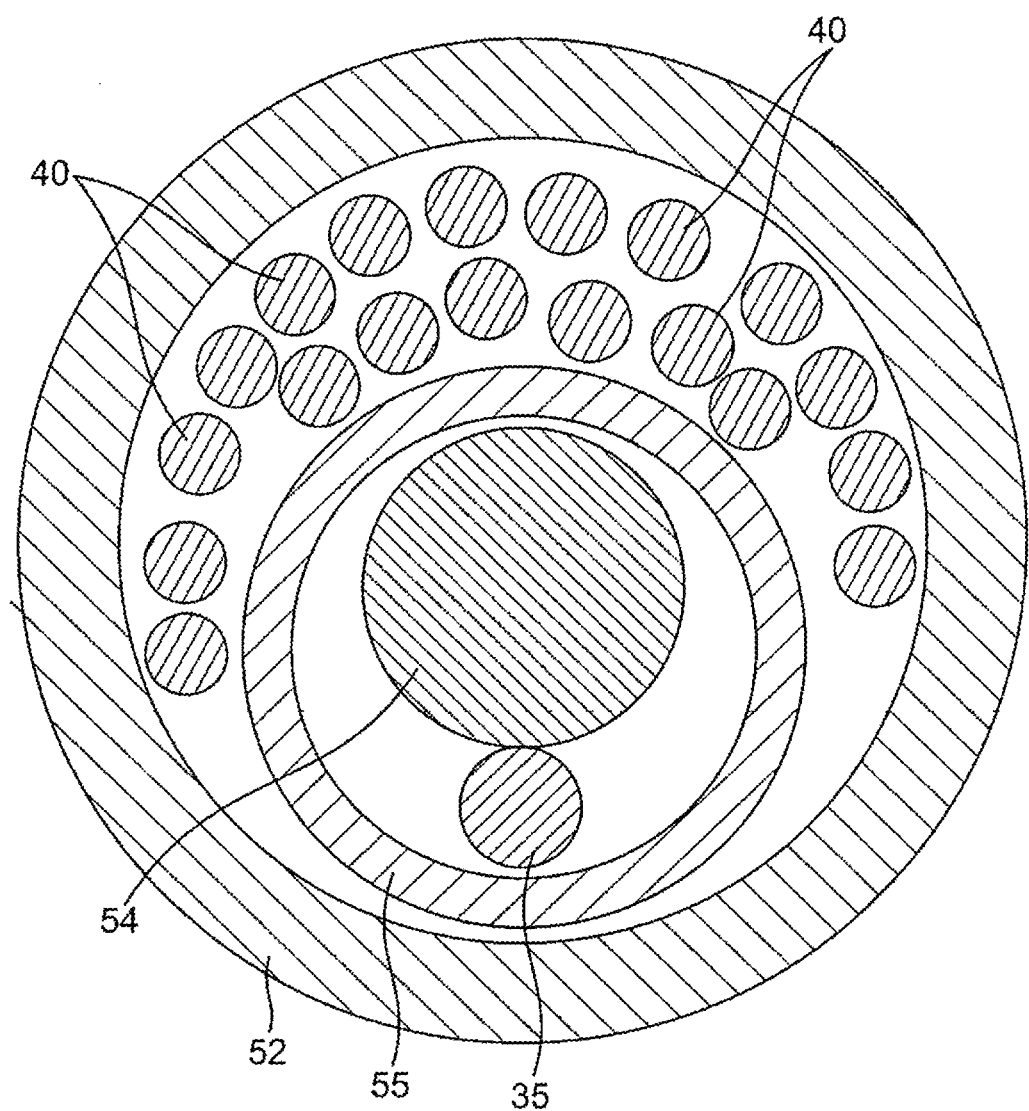
FIG. 6 is a longitudinal cross-sectional view of the mapping assembly of FIG. 3 along line 6-6.
Figure 7:
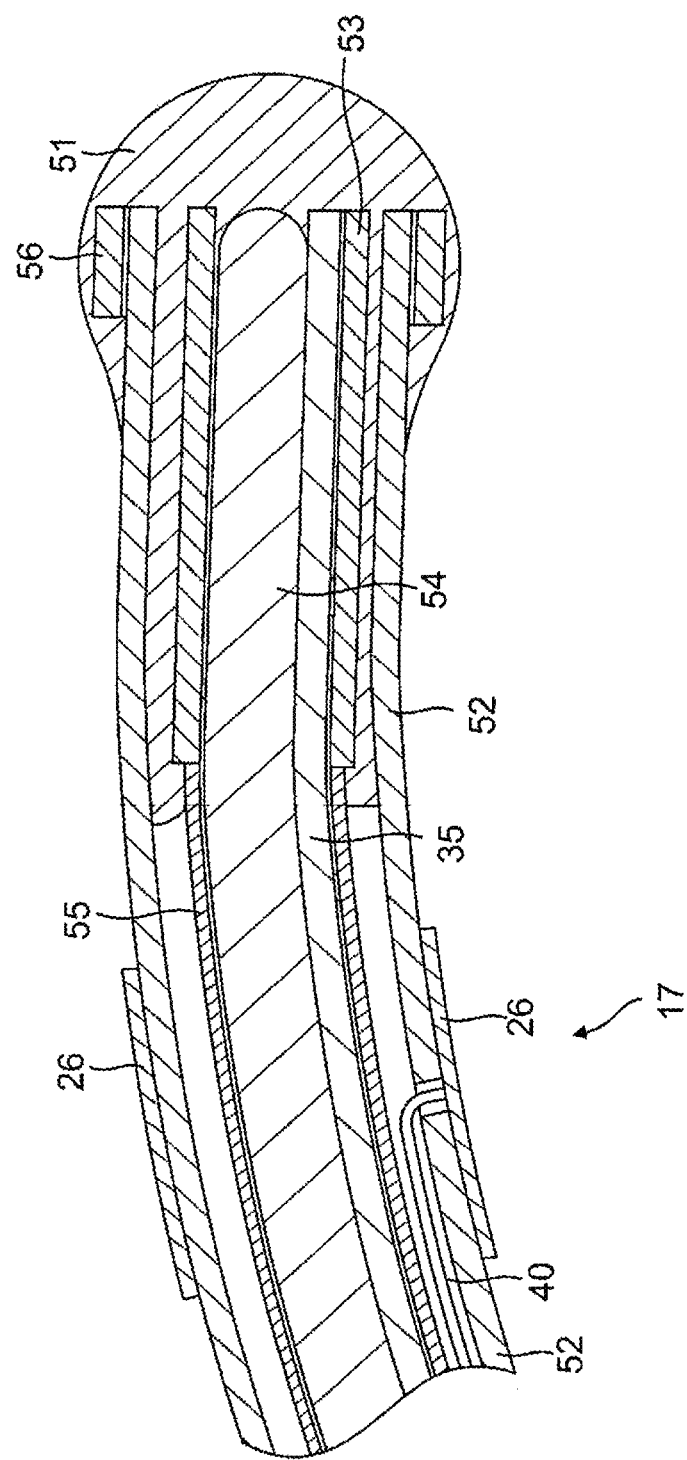
FIG. 7 is a side cross-sectional view of an embodiment of a distal end of the mapping assembly of FIG. 3.

The generally circular main region 39 is generally traverse, if not also perpendicular, to the catheter body 12 and the intermediate section 14. The generally circular main region 39 can form a flat circle or can be very slightly helical. The main region 39 has an outer diameter preferably ranging from about 10 mm to about 25 mm, more preferably about 12 mm to about 20 mm. The generally circular main region 39 can curve in a clockwise direction or a counter-clockwise direction. As shown in FIGS. 5, 6 and 7, the mapping assembly 17 is formed of a non-conductive cover or tubing 52 which can have any cross-sectional shape as desired. The non-conductive cover 52 can be made of any suitable material, and is preferably made of a biocompatible plastic such as polyurethane or PEBAX. The non-conductive cover 52 can be pre-formed into the desired generally circular shape of the generally circular main region 39. Alternatively, the shape of the generally circular main region 39 can be defined by a wire or other component extending through the non-conductive cover 52.

In the depicted embodiment, a pre-formed support member 54 extends through the non-conductive cover 52 to define the shape of the generally circular main region 39. The support member 54 is made of a material having shape-memory, i.e., that can be straightened or bent out of its original shape upon exertion of a force and is capable of substantially returning to its original shape upon removal of the force. A suitable material for the support member 54 is a nickel/titanium alloy. Such alloys typically comprise about 55% nickel and 45% titanium, but may comprise from about 54% to about 57% nickel with the balance being titanium. A suitable nickel/titanium alloy is Nitinol, which has excellent shape memory, together with ductility, strength, corrosion resistance, electrical resistivity and temperature stability.

A series of ring electrodes 26 are mounted on the non-conductive cover 52 of the generally circular main region 39 of the mapping assembly 17, as shown in FIG. 5. The ring electrodes 26 can be made of any suitable solid conductive material, such as platinum or gold, preferably a combination of platinum and iridium, and mounted onto the non-conductive cover 52 with glue or the like. Alternatively, the ring electrodes 26 can be formed by coating the non-conductive cover 52 with an electrically conducting material, like platinum, gold and/or iridium. The coating can be applied using sputtering, ion beam deposition or an equivalent technique. A suitable mapping assembly is described in U.S. Pat. No. 7,274,957, the entire disclosure of which is hereby incorporated by reference. If desired, additional electrodes (not shown) could be mounted along the intermediate section 14 and/or the generally straight proximal section 38.

The contraction puller member 35, for example, a contraction puller wire, is provided to contract the generally circular main region 39 to thereby change or reduce its diameter, for example, when mapping or ablating circular or tubular regions of the heart. The contraction wire 35 has a proximal end anchored in the control handle 16, which is used to manipulate the contraction wire as described further below. The contraction wire 35 extends through the central lumen 18 of the catheter body 12, through the third lumen 32 of the intermediate section 14 and into the non-conductive cover 52 of the mapping assembly 17. The portion of the contraction wire 35 extending through the non-conductive cover 52 is positioned on the side of the generally circular main region 39 closer to the center of the generally circular main region, as best shown in FIG. 6. The center of the generally circular main region refers to the center of the circle formed by the generally circular main region. With this arrangement, contraction of the generally circular main region 39 is dramatically improved over arrangements where the position of the contraction wire 35 is not so controlled.

As shown in FIGS. 5 and 6, within the mapping assembly 17, the contraction wire 35 extends through a plastic tube 55. In one embodiment, the plastic tube 55 comprise three layers, including an inner layer of polyimide over which a braided layer is formed, the braided layer comprising a braided stainless steel mesh or the like, as is generally known in the art. The braided layer enhances the strength of the plastic tube 55, reducing the tendency for contraction wire 35 to straighten the preformed curve of the mapping assembly 17. A thin plastic layer of polytetrafluoroethylene is provided over the braided layer to protect the braided layer from getting tangled with the lead wires 40 within the non-conductive cover 52. The plastic tube 55 has a proximal end anchored to the distal end of the intermediate section 14 in the third lumen 32 by glue or the like (FIG. 8a). The support member 54 extends through the plastic tube 55 with the contraction wire 35 (FIG. 8a). The distal ends of the support member 54 and the contraction wire 35 are soldered or otherwise attached to a small stainless steel tube 53 (FIG. 7). With this arrangement, the relative positions of the contraction wire 35 and the support member 54 can be controlled so that the contraction wire can be positioned on the side of the generally circular region 39 closer to the center of the generally circular region 39, as described above. The contraction wire 35 on the inside of the curve pulls the support member 54 to the inside of the curve, enhancing contraction of the generally circular region 39. Further, when the plastic tube 55 includes a braided layer, it keeps the contraction wire 35 from tearing through the non-conductive cover 52.

A third compression coil 46 is situated within the catheter body 12 and intermediate section shaft 14 in surrounding relation to the contraction wire 35 (FIG. 2a). The third compression coil 46 extends from the proximal end of the catheter body 12 and to near the distal end of the third lumen 32 of the intermediate section 14. The third compression coil 46 is made of any suitable metal, such as stainless steel, and is tightly wound on itself to provide flexibility, i.e., bending, but to resist compression. The inner diameter of the third compression coil 46 is preferably slightly larger than the diameter of the contraction wire 35. The outer surface of the compression coil 46 is covered by a flexible, non-conductive sheath 68, e.g., made of polyimide tubing. The third compression coil 46 preferably is formed of a wire having a square or rectangular cross-sectional area, which makes it less compressible than a compression coil formed from a wire having a circular cross-sectional area. As a result, the third compression coil 46 keeps the catheter body 12, and particularly the intermediate section 14, from deflecting when the contraction wire 35 is manipulated to contract the mapping assembly 17 as it absorbs more of the compression.

The third compression coil 46 is anchored at its proximal end to the outer wall 20 of the catheter body 12 by the proximal glue joint 50 and to the intermediate section 14 by distal glue joint 72.

It is understood that glue joints throughout the catheter 10 may comprise polyurethane glue or the like. The glue may be applied by means of a syringe or the like through a hole made in the tubing walls. Such a hole may be formed, for example, by a needle or the like that punctures the tubing walls where the needle is heated sufficiently to form a permanent hole. The glue is then introduced through the hole to wick around the component(s) within the tubing to form a glue joint about the entire circumference of the component(s).

In the depicted embodiment of FIG. 7, the distal end of the mapping assembly 17 is sealed closed with a dome 51 of polyurethane glue or the like. A short ring 56, made of metal or plastic, and preferably polyamide, is mounted within the distal end of the non-conductive cover 52. The short ring 56 prevents the distal end of the non-conductive cover 52 from collapsing, there by maintaining the diameter of the non-conductive cover at its distal end.

At the junction of the intermediate section 14 and the mapping assembly 17 as shown in FIGS. 8a and 8b, the non-conductive cover 52 is attached to the intermediate section 14 by glue or the like. The plastic tube 55 has its proximal end inserted and glued in the distal end of the intermediate section 14. The glue (not shown) from the plastic tube 55 can further serve to anchor the distal end of the third compression coil 46 in place within the third lumen 32. The support member 54 extends from the third lumen 32 into the plastic tube 55 within the non-conductive cover 52. The proximal end of the support member 54 terminates a short distance proximally from the distal end of the third lumen 32, approximately about 5 mm, so as not to adversely affect the ability of the intermediate section 14 to deflect. However, if desired, the proximal end of the support member 54 can extend proximally further into the intermediate section 14 and/or the catheter body 12.

The lead wires 40 attached to the ring electrodes 26 extend through the first lumen 30 of the intermediate section 14 (FIG. 2a), through the central lumen 18 of the catheter body 12, through the control handle 16, and terminate at their proximal end in a connector (not shown) which is connected to an appropriate monitor or other device for receiving and displaying the information received from the ring electrodes 26. The portion of the lead wires 40 extending through the central lumen 18 of the catheter body 12, control handle 16 and proximal end of the intermediate section 14 is enclosed within a protective sheath 62, which can be made of any suitable material, preferably polyimide.

The protective sheath 62 is anchored at its distal end to the proximal end of the intermediate section 14 by gluing it in the lead wire lumen 30 with polyurethane glue or the like to form glue joint 73.

The lead wires 40 are attached to the ring electrode 26 by any conventional technique. In one embodiment, each ring electrode 26 is mounted by first forming a hole in the non-conductive cover 52. An electrode lead wire 40 is fed through the hole, and the ring electrode 26 is welded in place over the lead wire and non-conductive cover 52.

With reference to FIG. 1, the control handle 16 comprises a generally elongated handle housing, which can be made of any suitable rigid material, such as plastic configured through a suitable molding process. In the illustrated embodiment, the housing includes two opposing halves 16a and 16b that generally mirror each other and are joined by glue, sonic welding or other suitable means along a longitudinal peripheral seam 28 around the housing. In the illustrated embodiment, the cross section of the handle 16 formed by the opposing halves changes along the length of the handle. A more distal portion 112 has a smaller, generally rectangular cross section. A mid-portion 114 has a larger, generally rectangular cross section. A more proximal portion 116 has a generally circular cross section.

Figure 9:
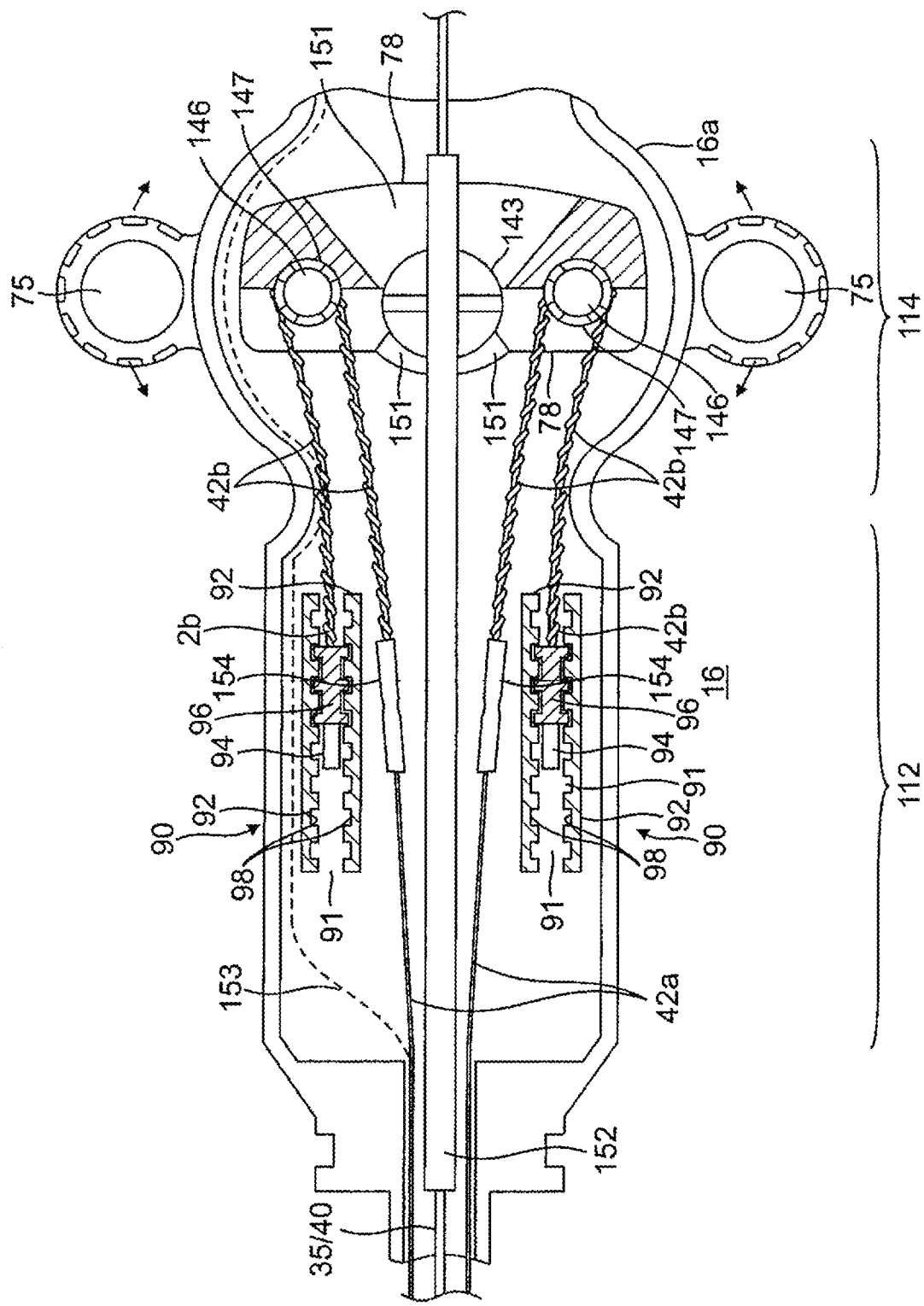
FIG. 9 is a top plan view of an embodiment of a control handle housing half including an embodiment of a deflection control assembly.
Figure 10:
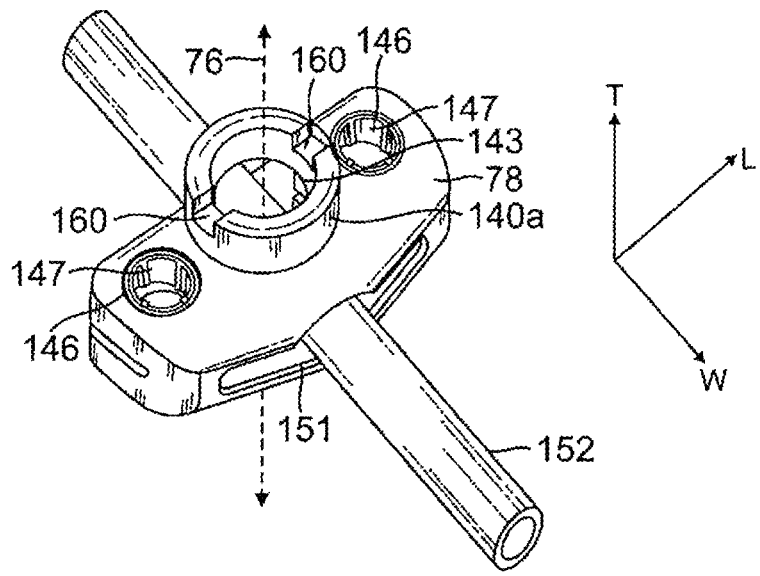
FIG. 10 is a top perspective view of an embodiment of a rocker member of a deflection control assembly.
Figure 11:
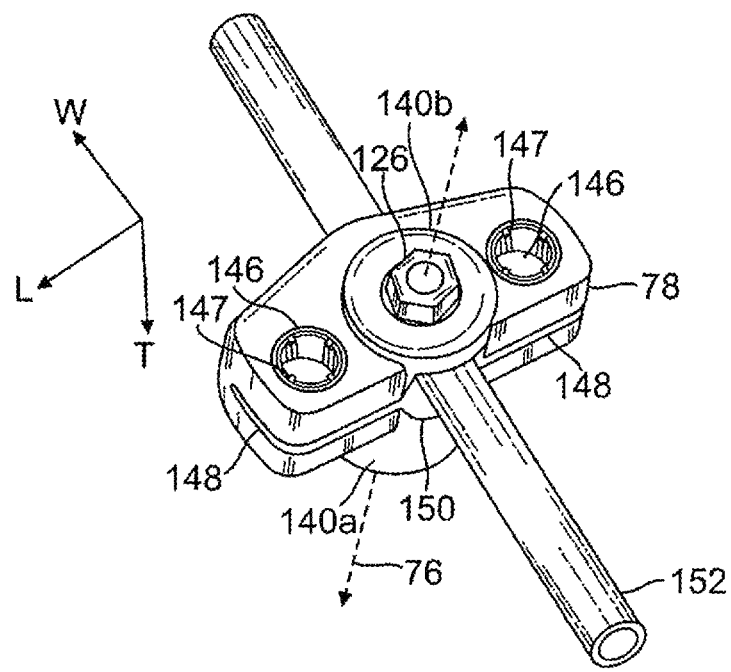
FIG. 11 is a bottom perspective view of an embodiment of a rocker member.

In the illustrated embodiment of FIGS. 1 and 9, the control handle 16 houses components of a deflection control assembly 74 in the mid-portion 114. The deflection control assembly includes a deflection member or arm 75 that can be directly manipulated by an operator to control deflection of the intermediate section 14. The deflection arm 75 is rotatable about an axis 76 that is generally transverse or perpendicular to the longitudinal axis of the control handle. The deflection control assembly 74 has a rotatable rocker member 78 that acts on the deflection puller members 42 to deflect the intermediate section 14. The rocker member 78 has a length L dimension, a width W dimension and a thickness T dimension (FIGS. 10 and 11).

Figure 12:
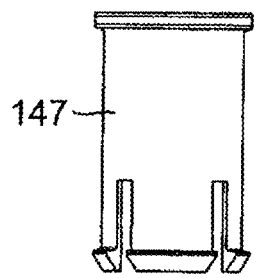
FIG. 12 is a side view of an embodiment of a pulley of a deflection control assembly.

Along its thickness dimension T, the rocker member 78 is configured with two opposing annular formations 140a and 140b that define a central hole or passage 143 that extends through its entire thickness. The central hole 143 is aligned with the rotational axis 76 of the deflection arm 75. Along its length dimension L, the rocker member 78 also has two smaller holes 146 that oppose each other across the central hole 143. In each hole sits a pulley 147, for example, a snap bearing (FIG. 12), that has a rotational axis parallel to the axis 76. Each deflection puller member 42 enters the rocker member through slots 148 and a portion is wound around a respective pulley 147.

As understood by one of ordinary skill in the art, the rocker member 78 and the pulleys 147 are arranged such that rotation of the rocker member in one direction about the axis 76 draws back one puller member 42 to deflect the intermediate section 14 in that direction. With reference to FIGS. 13a-13c, as the rocker member 78 is rotated by means of the deflection arm (as represented by line 75), the pulleys 147 are displaced from a neutral position (FIG. 13a) with one pulley 147 drawing a puller member 42 on one side of the catheter body 12 against its anchored proximal end for deflecting the intermediate section 14 toward that side (FIGS. 13b and 13c).

Each deflection puller member 42 may comprise multiple segments. As illustrated in FIG. 9, each deflection puller member has a distal puller wire 42a and a proximal fiber 42b that are joined or connected at a location within the control handle 16 distal the rocker member 78. The puller wire 42a and the tensile fiber 42b of each deflection puller member are connected or secured to each other by a connector 154, e.g., a crimped brass ferrule covered by shrink tubing. Each puller wire 42a extends through the catheter body 12 and the intermediate section 14. Each tensile fiber 42b extends inside the control handle 16. In this manner, it is the more flexible tensile fibers 42b that interact with the pulleys 147 and undergo repeated bending and straightening during deflection operations, as they are less prone to bending stress and fatigue failure.

Each puller wire 42a is made of any suitable metal, such as stainless steel or Nitinol. Preferably each puller wire has a low friction coating, such as a coating of Teflon® or the like. Each puller wire has a diameter preferably ranging from about 0.006 inch to about 0.012 inch. Preferably both of the puller wires have the same diameter. Flat puller wires may be used in place of round puller wires. Their cross sectional dimensions should be such that they provide comparable tensile strengths as round puller wires.

Each tensile fiber 42b may be of a high modulus fiber material, preferably having an ultimate tensile strength substantially in the range of 412-463 ksi (2480-3200 Mpa) such as High Molecular Density Polyethylene (e.g., Spectra™ or Dyneema™), a spun para-aramid fiber polymer (e.g., Kevlar™) or a melt spun liquid crystal polymer fiber rope (e.g., Vectran™), or a high strength ceramic fiber (e.g., Nextel™). The term fiber is used herein interchangeably with the term fibers in that the tensile fiber may be of a woven or braided construction. In any case, these materials tend to be flexible, providing suitable durability when used in wrapped engagement with the pulleys and the like for greater throw in deflecting the catheter tip. Further, they are substantially non-stretching, which increases the responsiveness to the manipulation of the control handle, and nonmagnetic so that they generally appear transparent to an MRI. The low density of the material causes it to be generally transparent to an x-ray machine. The materials can also be nonconductive to avoid shorting. Vectran™, for example, has high strength, high abrasion resistance, is an electrical insulator, nonmagnetic, is polymeric, and has low elongation under sustained loading conditions.

In the illustrated embodiment of FIG. 9, each tensile fiber 42b extends proximally from the connector 154 toward the rocker member 78 where each is wound around a respective pulley 147 and turns about 180 degrees to double back toward the distal end of the control handle. Each proximal end of the tensile fiber 42b is anchored by an anchor assembly 90 that includes a pair or racks 92, a slug 94 and a stop 96. The proximal end of each tensile fiber 22b extends between a channel 91 defined by the pair of racks 92, and the proximal end of each tensile fiber is encased within a molded member or slug 94 sized to fit in and translate in the channel 91. Proximal the slug are the stops 96 that are adjustably positioned in a selected location along the racks 92, for example, by means of interlocking teeth 98 formed in the racks and the stops to releasably lock in the selected position against movement. The stops 96 are formed so that each respective tensile fiber 42b can slide through or below them while blocking the slugs 94 from moving proximally past them. Accordingly, the stops 96 limit the proximal movement of the slugs 94 and anchor the proximal ends of the tensile fibers 42b to effectuate deflection when each is drawn proximally by the deflection control assembly 74. During assembly of the control handle 16, before the two housing halves 16a, 16b are joined, the stops 96 are selectively positioned between the racks 92 to achieve a desirable tension in each tensile member. The interlocking teeth 98 of the racks 92 and stops 96 allow for fine adjustments in setting the tension.

Figure 14:
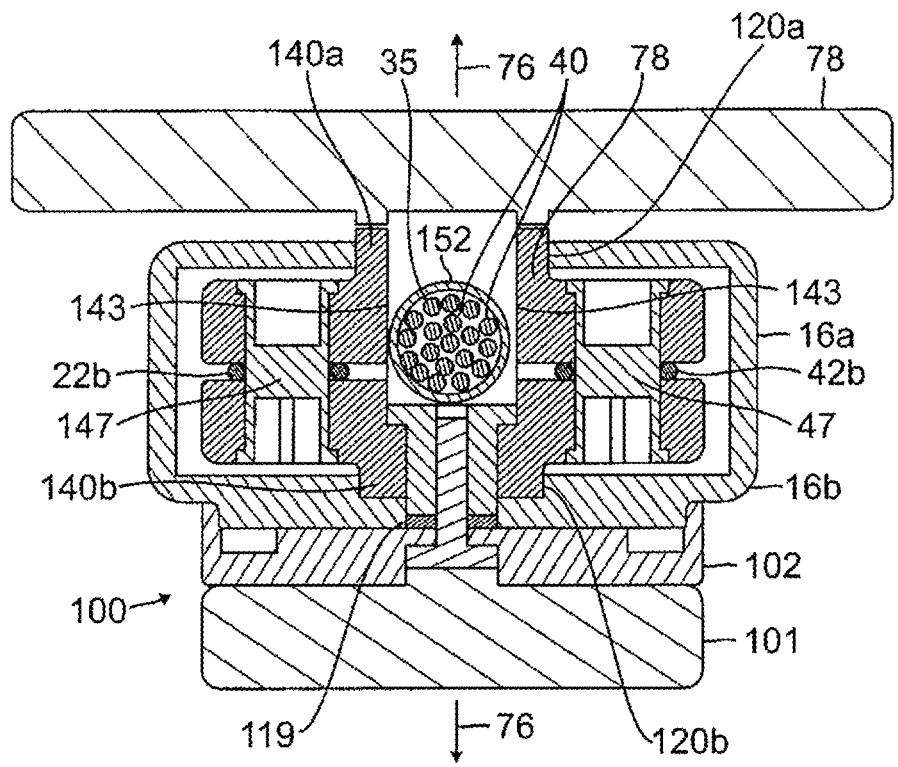
FIG. 14 is a longitudinal cross section of an embodiment of the deflection control assembly and tension control assembly mounted on a control handle.
Figure 14A:
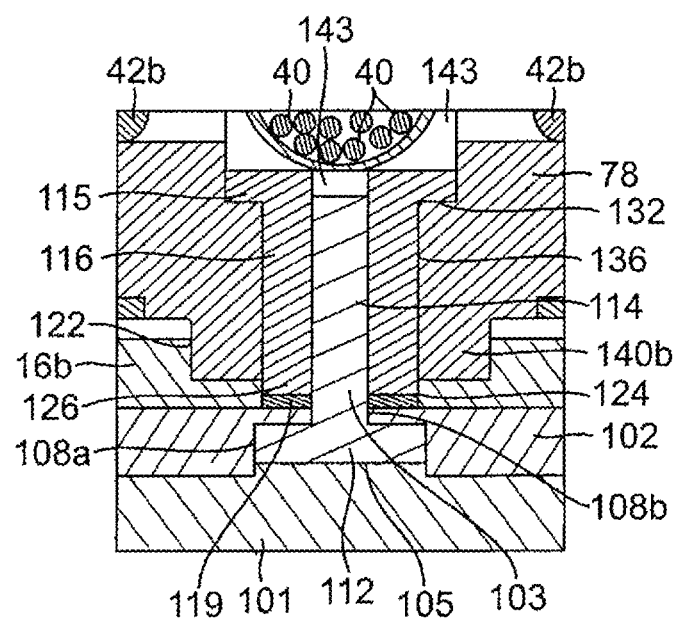
FIG. 14a is a detailed view of a portion of FIG. 14, including an embodiment of a retaining nut and a tension screw.

The construction and assembly of the deflection control assembly 74 including the deflection arm 75 and a tension adjustment member 101 on the control handle 16 are described as follows. With reference to FIGS. 14 and 14a, the rocker member 78 of the assembly 74 is situated between the two halves 16a and 16b of the control handle 16, with each of its annular formations 140a and 140b extending respectively through an opening 120a, 120b formed in the distal portion 114 of each housing half 16a and 16b.

Figure 15:
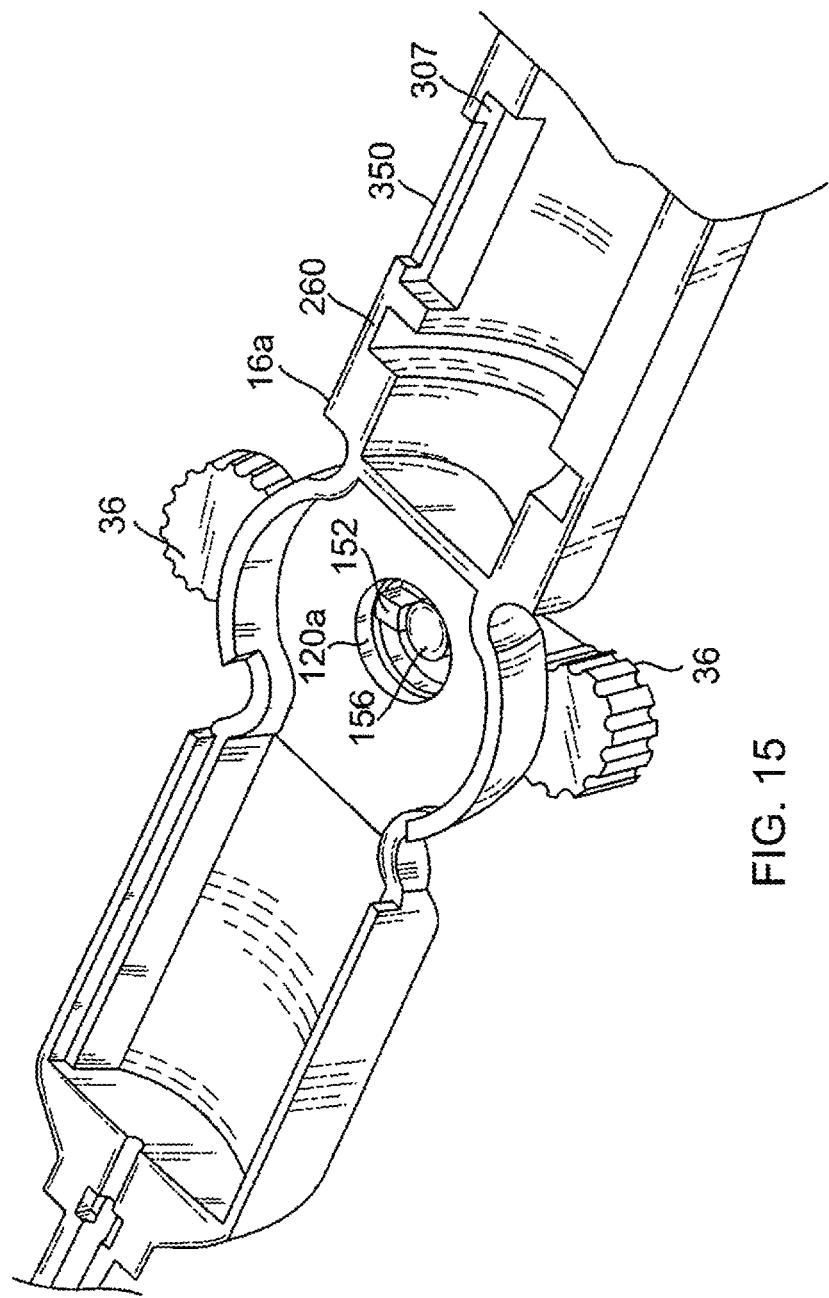
FIG. 15 is a partial perspective view of an embodiment of a first control handle housing half.
Figure 16:
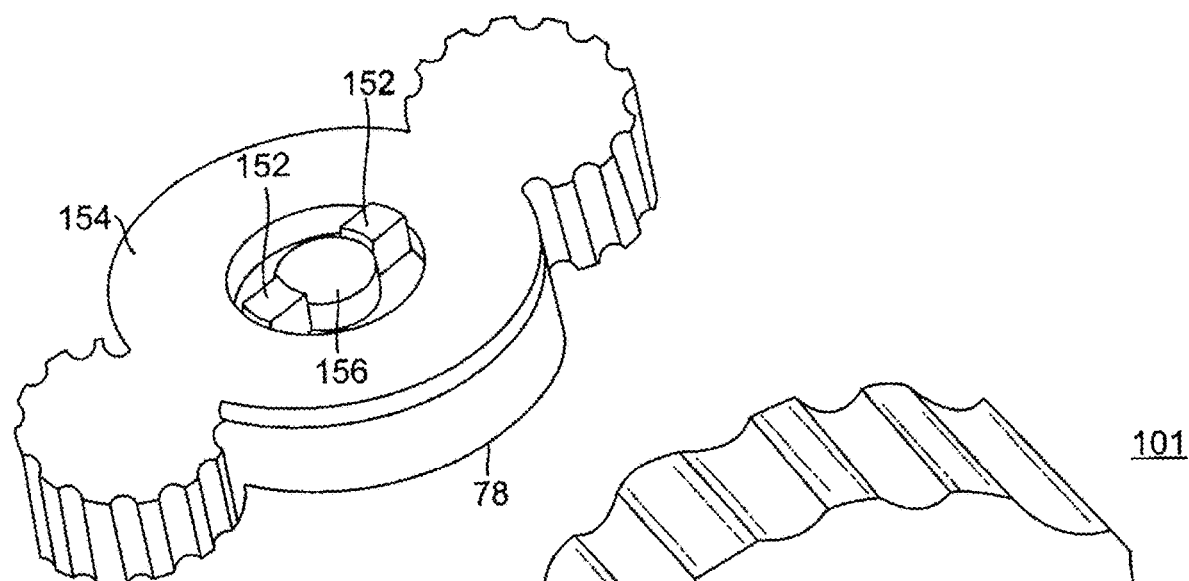
FIG. 16 is a perspective view of an embodiment of a deflection arm.

The annular formation 140a has recesses 160 (FIG. 10) exposed through the opening 120a (FIG. 15) that receive protrusions 152 projecting from a facing surface 154 of the deflection arm 75 (FIG. 16) to rotationally couple the deflection arm 75 and the rocker member 78. The protrusions 152 can snap fit into the recesses 160 and/or be secured by adhesives, glue, sonic welding and the like. A central circular protrusion 156 from the deflection arm 75 fits into the hole 143 circumscribed by the annular formation 140a of the rocker member 78. A suitable deflection assembly and control handle are described in co-pending U.S. application Ser. No. 12/346,834, filed Dec. 30, 2008, entitled DEFLECTABLE SHEATH INTRODUCER, the entire disclosure of which is hereby incorporated by reference. Another suitable deflection assembly with deflection sensitivity is described in co-pending U.S. application Ser. No. 12/211,728, filed Sep. 16, 2008, entitled CATHETER WITH ADJUSTABLE DEFLECTION SENSITIVITY, the entire disclosure of which is hereby incorporated by reference. Therein, a cam that is responsive to a deflection sensitivity knob can vary the separation distance between the two pulleys 147, thereby changing the deflection sensitivity of the deflection arm.

Opposing the deflection arm 75 is the deflection tension adjustment member or dial 101 (FIGS. 17 and 20) which is coupled to and indirectly engaged with the rocker member 78 by various mechanisms and parts and allows an operator to adjust the ease with which the deflection arm 75 can be rotated. Mounted primarily on the housing half 16b, the illustrated embodiment of a tension adjustment assembly 100 includes the adjustment dial 101 (FIG. 17), a locking plate 102 (FIG. 18), a tension cap screw 103, a retaining nut 136 and a washer 119 (see FIGS. 14 and 14a). A user rotates the dial 101 to adjust the tightness or tension of the rotational movement of deflection arm 75 by effectively compressing or releasing the rocker member 78 against the washer 119 (e.g., a Belleville type) and the control handle housing half 16b.

Figure 17:
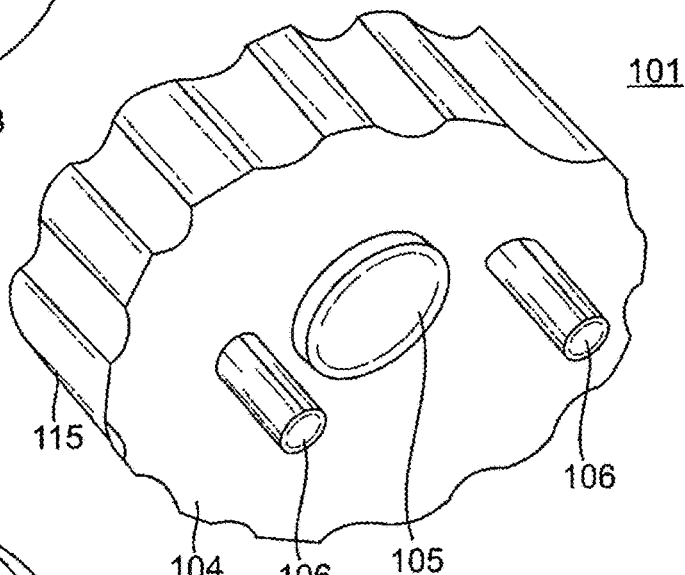
FIG. 17 is a perspective view of an embodiment of a tension control dial.
Figure 18:
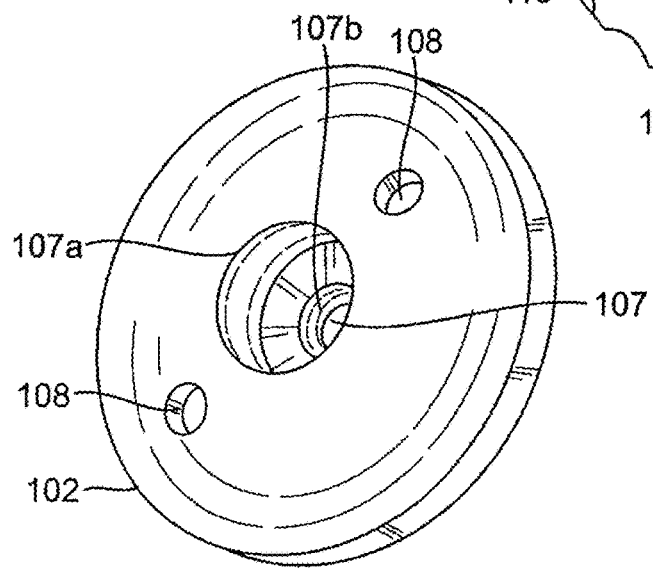
FIG. 18 is a perspective view of an embodiment of a locking plate.

The dial 101 has a generally circular cross section with a circumferential edge 115 having a friction-inducing surface (FIG. 17). A central circular protrusion 105 and a plurality of prongs 106 (FIG. 17) situated along a diameter of the dial project from a surface 104 of the dial 101.

Figure 19:
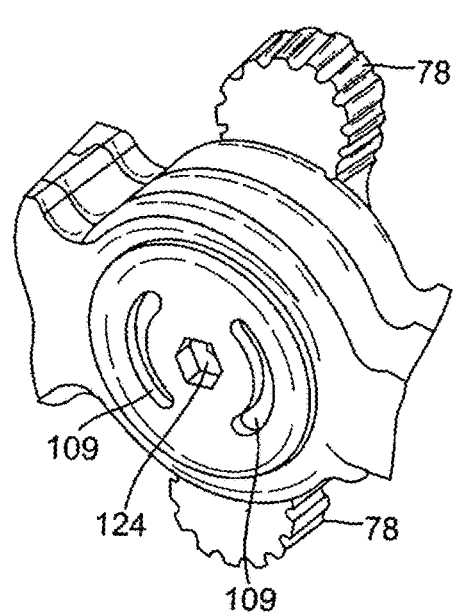
FIG. 19 is a partial perspective view of a portion of an embodiment of a control handle.
Figure 20:
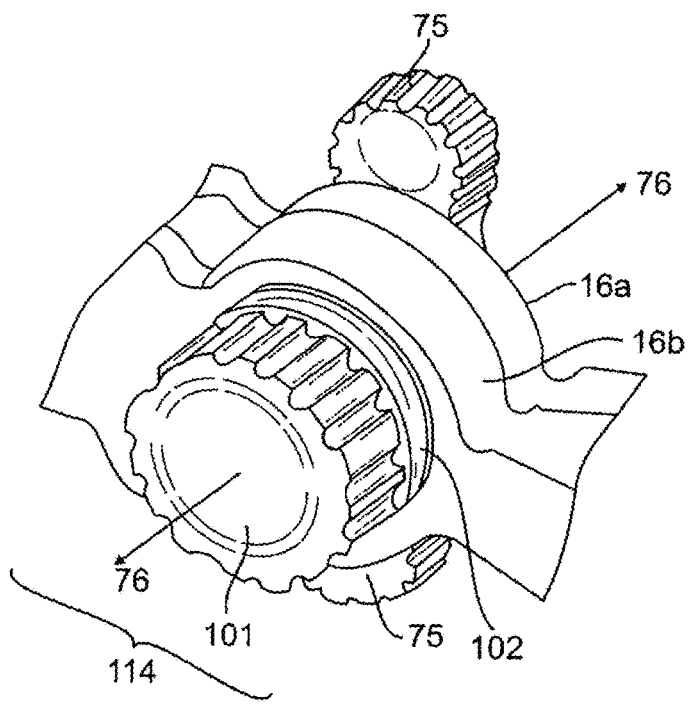
FIG. 20 is a partial perspective view of a portion of an embodiment of a deflection arm and a tension control member mounted on a control handle.
Figure 21:
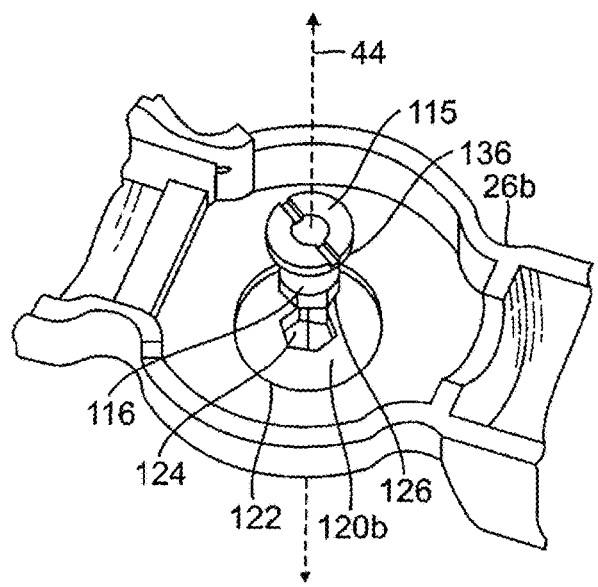
FIG. 21 is a partial perspective view of a portion of an embodiment of a second control handle housing half and a retaining nut, the second control housing half adapted to oppose the first control handle housing half.
Figure 22:
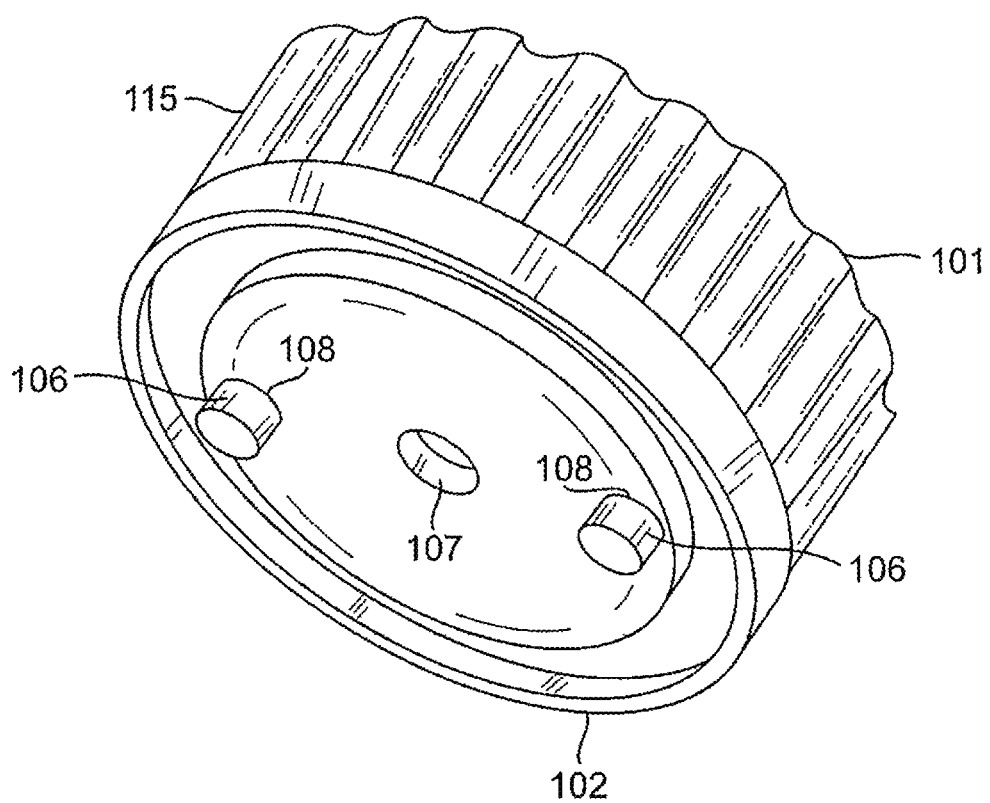
FIG. 22 is a perspective view of the tension control dial of FIG. 17 and locking plate of FIG. 18 as assembled.

The locking plate 102 is sandwiched between the dial 101 and the handle housing 16b (FIG. 20). The locking plate 102 (FIG. 18) has a central larger hole 107 and two smaller holes 108, all three of which extend through the entire thickness of the locking plate. The two prongs 106 of the dial 101 are adapted to be inserted through the smaller holes 108 in the plate 102 (FIG. 21) and received in semi-circular grooves 109 (FIG. 19) formed in an outer surface of the housing half 16b. The grooves 109 limit the degree of rotation of the dial 101 in clockwise and counterclockwise directions. The central hole 107 of the plate 102 (FIG. 18) has different cross-sections that include a larger circular cross-section 107a and a smaller circular cross-section 107b. The larger circular cross-section 107a receives a head 112 of a cap screw 103, and the smaller circular cross-section 107b receives a threaded body 115 of the cap screw 103 (FIG. 14a).

The threaded body 115 of the cap screw 103 extending through the central hole 107 of the locking plate 102 engages the retaining nut 136 situated in the opening 143 of the rocker member 78. A head 115 of the nut abuts and is anchored against a neck 132 formed in the inner surface of the opening 143 of the rocker member 78. The opening 120b in the housing half 16b (FIG. 21) has a larger cross section 122 and a smaller cross section 124. The smaller cross section 124 has a polygonal shape which matches a polygonal (e.g., hexagonal) end 126 of the nut 136 so that the nut 136 is effectively locked against rotation relative to the housing handle 16b.

The central protrusion 105 of the dial 101 (FIG. 17) forms a press or interference fit with the head 112 of the cap screw 103 to create rotational alignment between these two components. The prongs 106 of the dial 101 lock and rotationally couple the dial 101 and the lock plate 102, and the cap screw 103 is rotationally coupled to the locking plate 102. Coupling of the dial 101 and the locking plate 102 may also be achieved by means of welding the two components together. In that case, the prongs 106 need not protrude from the dial 101 but can instead extend from the locking plate 102.

Between the polygonal end 126 of the nut 136 and the housing handle 16b is the washer 119 whose compression against the nut 136 and the housing handle 16b is adjustable by the user's rotation of the dial 101 which tightens or releases the engagement between cap screw 103 and the nut 136, thus increasing or decreasing the ease with which the rocker member 78 and hence the deflection arm 75 can be rotated.

Components that extend through the control handle, including, for example, the lead wires 40 and the contraction wire 35 also enter the control handle at the distal end. In the illustrated embodiment of FIG. 9, these components extend along the longitudinal axis of the control handle. A protective tubing 152 through which the components extend can be provided, positioned between the two deflection puller members 42 and through a channel 150 form through the width dimension W of the rocker member 78 (FIG. 11). Distal and proximal portions of the channel 150 have indents, e.g., triangular or wedge-shaped, 151 (FIGS. 9 and 11) to allow the rocker member 78 to rotate freely within a predetermined range of angles, e.g., about ±45 degrees of the longitudinal axis of the control handle 16, without interference by the tubing 152 and the components therethrough.

Alternatively, the components extending through the control handle, with the exception of the contraction wire 35, are routed on an off-axis path 153 diverging from the deflection puller members 42 at entry into the distal end of the control handle 16. The components thus extend along the periphery of the housing handle, bypassing the rocker member 78.

It is understood that the distance between the distal end of the compression coils 44 and the distal anchor sites of each deflection puller members 42 in the intermediate section 14 determines the curvature of the intermediate section 14 in the direction of the deflection puller members. For example, an arrangement wherein the two deflection puller members 42 are anchored at different distances from the distal ends of the compression coils 44 allows a long reach curve in a first plane and a short reach curve in a plane 90.degree. from the first, i.e., a first curve in one plane generally along the axis of the intermediate section 14 before it is deflected and a second curve distal to the first curve in a plane transverse, and preferably normal to the first plane. The high torque characteristic of the catheter intermediate section 14 reduces the tendency for the deflection in one direction to deform the deflection in the other direction. Suitable deflection control handles and parts thereof for use with such a catheter are described in U.S. patent application Ser. No. 08/924,611, filed Sep. 5, 1997, entitled "Omni-Directional Steerable Catheter", Ser. No. 09/130,359, filed Aug. 7, 1998, entitled "Bi-Directional Control Handle for Steerable Catheter", and Ser. No. 09/143,426, filed Aug. 28, 1998, entitled "Bidirectional Steerable Catheter with Bidirectional Control Handle", the entire disclosures of which are hereby incorporated by reference.

Figure 23:
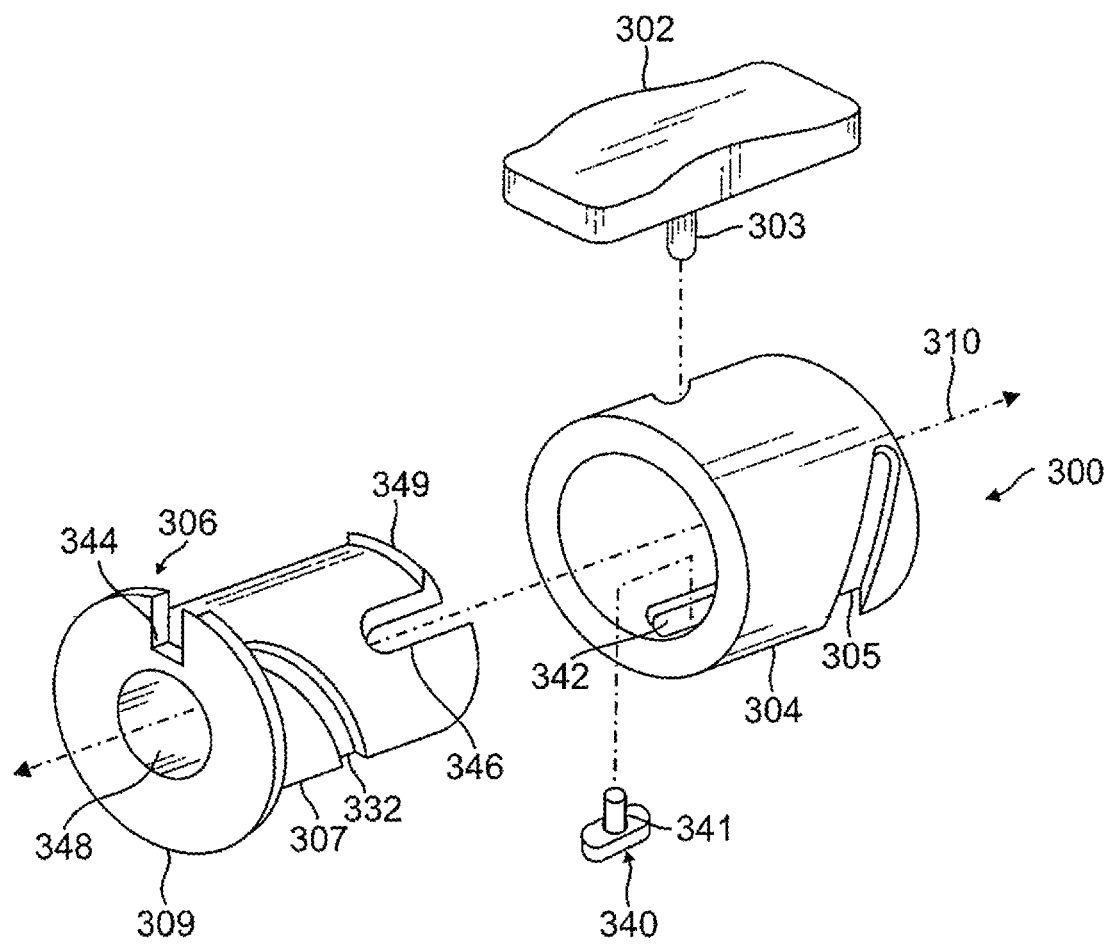
FIG. 23 is an exploded perspective view of an embodiment of a linear control assembly.

For adjusting the mapping assembly 17 by means of a third puller member, e.g., the contraction wire 35, a distal end of the contraction wire extending between the two deflection puller members 42 within the control handle 16 is anchored in the control handle for actuation by means of a linear control assembly 300 housed in the proximal portion 116 of the control handle. In the illustrated embodiment of FIG. 23, the linear control assembly 300 includes a linear control member 302, a fixed cam 306 whose body 307 supports a rotational member 304, the combination of which effectuates longitudinal movement of the contraction wire 35 relative to the catheter body 12, for example, to contract and expand the mapping assembly 17. In the disclosed embodiment, the linear control assembly 300 is positioned proximal the deflection control assembly 74, although it is understood that it can be positioned distal the deflection control assembly 74.

With reference to FIGS. 23-27, the proximal portion 116 of the control handle 16 in which the linear control assembly is housed has a generally circular cross section of an inner diameter D1 and an outer diameter D2. The cam 306 has a collar 309 and a barrel body 307. The collar is sized so that it can be received in an inner circumferential groove 260 (FIG. 15) formed in the control handle housing halves 16a and 16b. The collar is affixed therein by glue or the like so the cam is fixed relative to the control handle 16. The rotational member 304 is mounted on the body 307 of the cam 36 so that it can rotate on the cam in response to linear movement of the control member 302 along a longitudinal axis 310 of the control handle.

Figure 24:
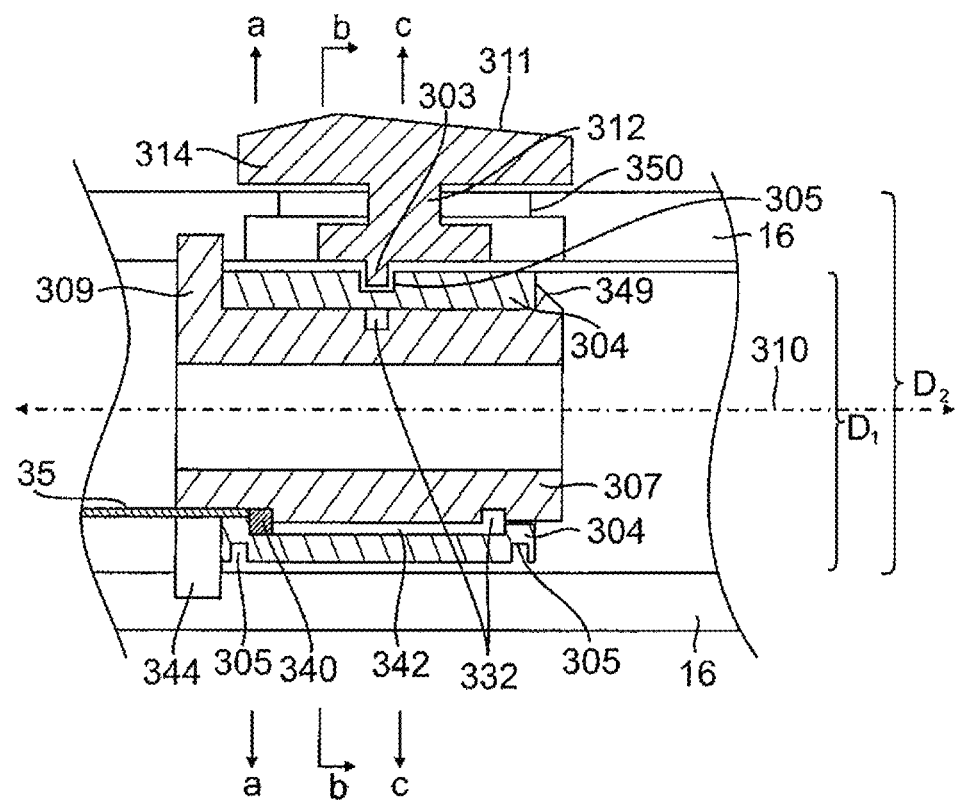
FIG. 24 is a side cross-sectional view of the linear control assembly of FIG. 23, as assembled on a control handle.
Figure 25:
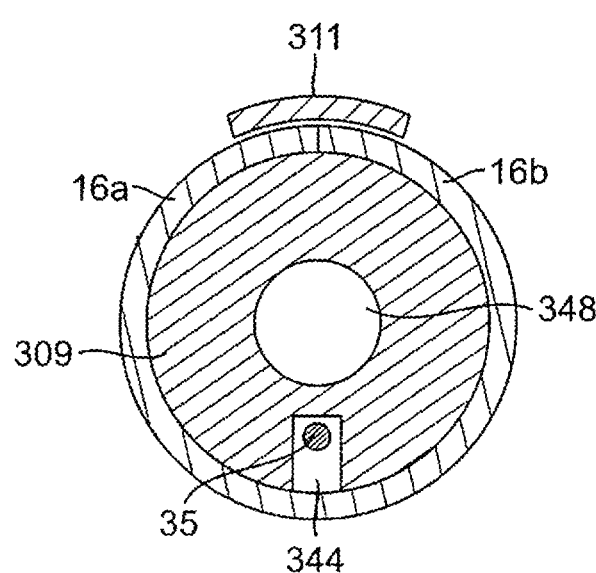
FIG. 25 is a longitudinal cross-sectional view of the linear control assembly of FIG. 24, taken along line a-a.
Figure 26:
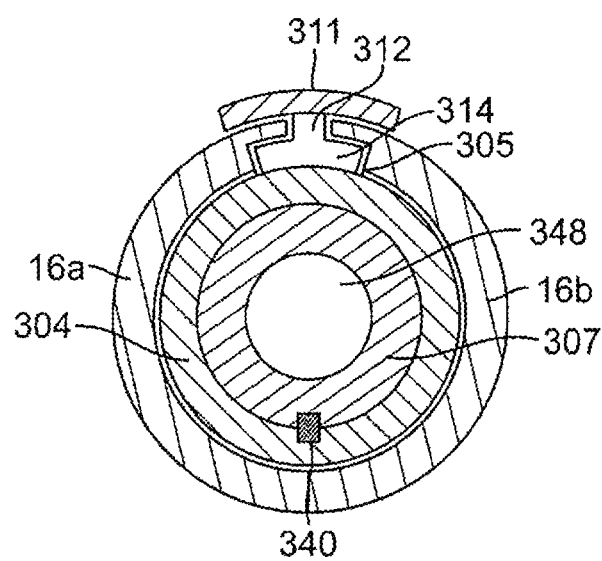
FIG. 26 is a longitudinal cross-sectional view of the linear control assembly of FIG. 24, taken along line b-b.
Figure 27:
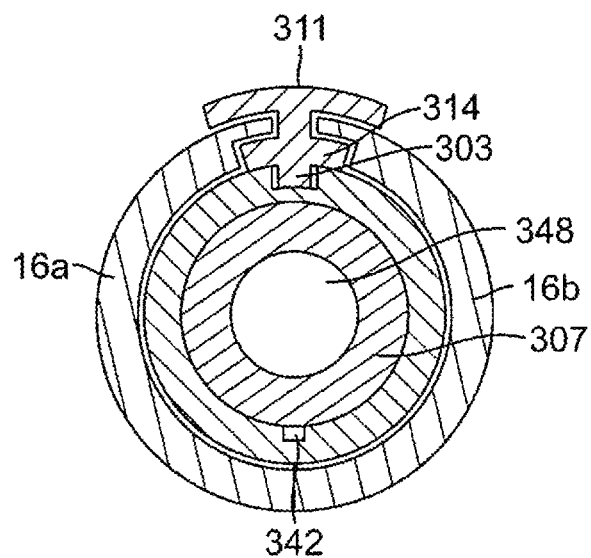
FIG. 27 is a longitudinal cross-sectional view of the linear control assembly of FIG. 24, taken along line c-c.
Figure 28:
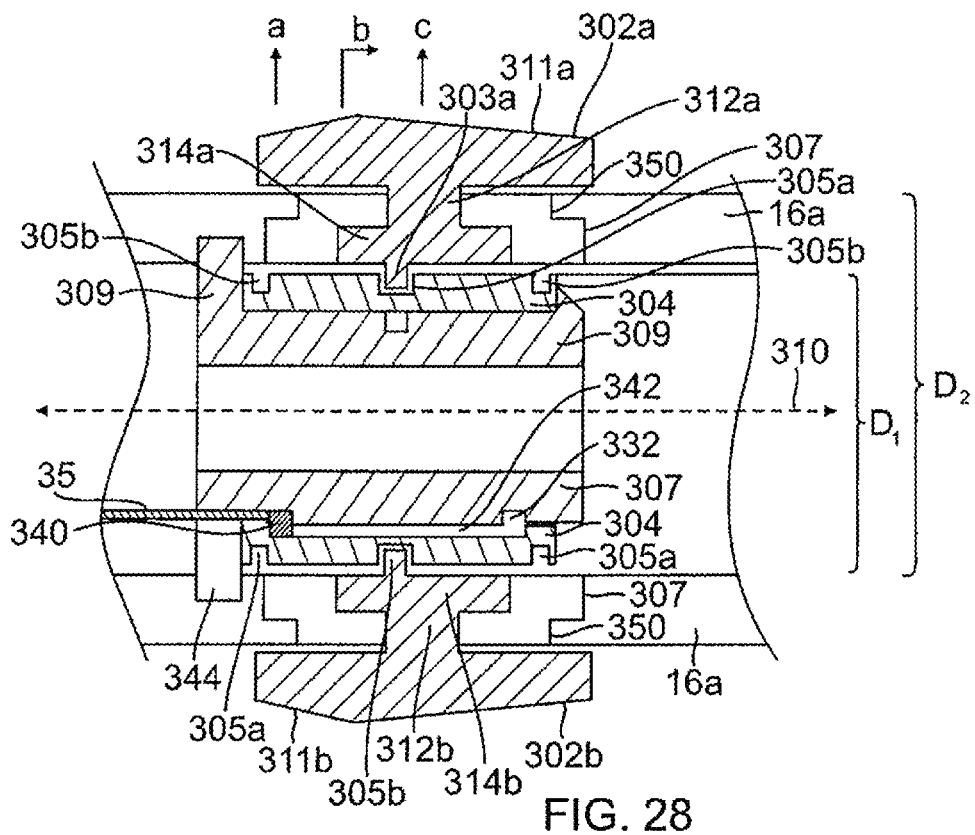
FIG. 28 is a side cross-sectional view of an alternate embodiment of the linear control assembly, as assembled on a control handle.
Figure 29:
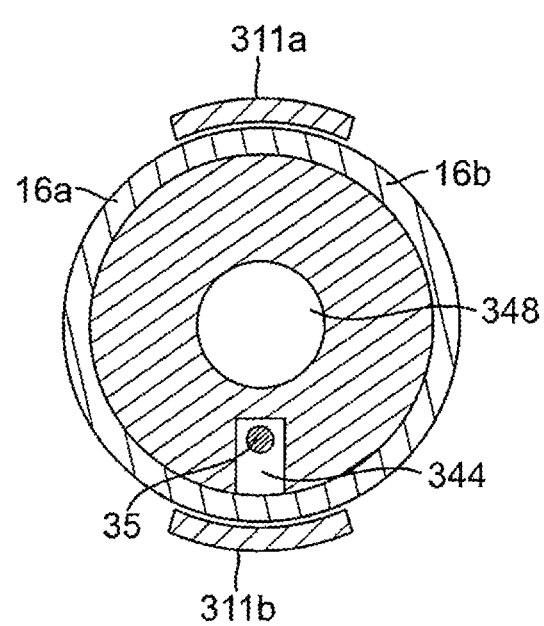
FIG. 29 is a longitudinal cross-sectional view of the linear control assembly of FIG. 28, taken along line a-a.
Figure 30:
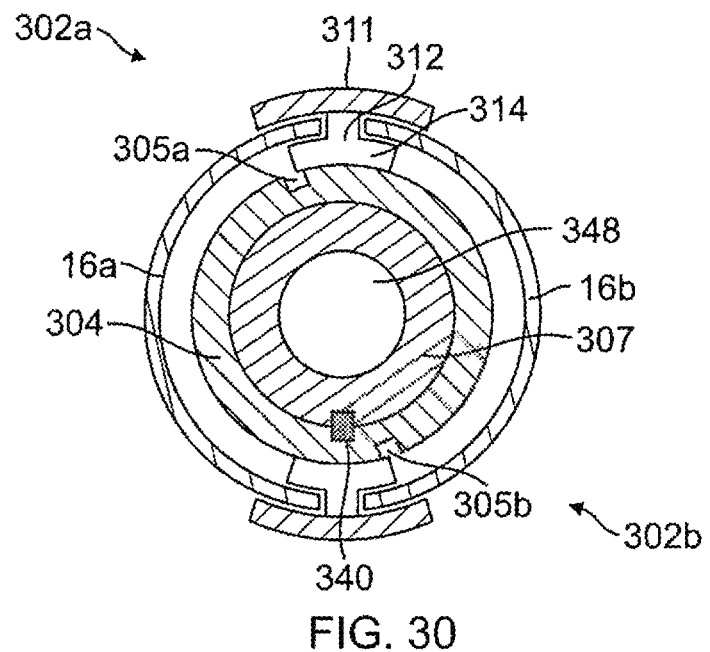
FIG. 30 is a longitudinal cross-sectional view of the linear control assembly of FIG. 28 taken along line b-b.
Figure 31:
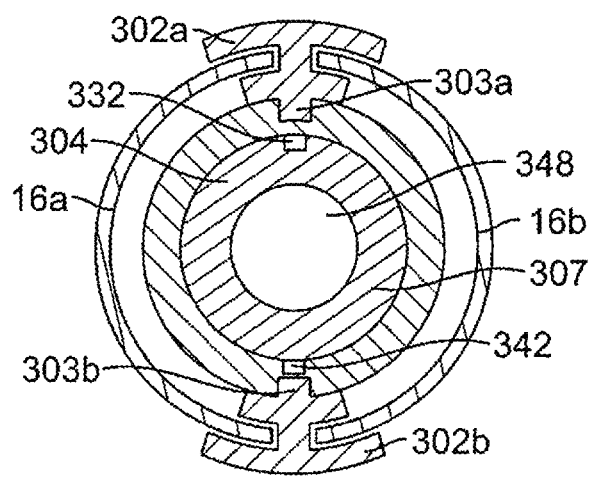
FIG. 31 is a longitudinal cross-sectional view of the linear control assembly of FIG. 28, taken along line c-c.

To convert linear movement of the linear control member 302 into rotational movement of the rotational member 304, the member 304 has a helical track 305 formed in its outer surface that extends between a distal end and a proximal end of the member 304. The linear control member 302 has an outer portion 311, a thinner portion 312, a wider portion 314, and a projection 303 (FIG. 24). To couple the control member and the inner rotational member, the projection 303 is received in the track 305 through an opening formed by a recess opening 350 (FIG. 15) formed in each control handle housing halves 16a, 16b for the thinner portion 312. The wider portion 314 has a width dimension (better seen in FIGS. 26 and 27) that conforms to a cutout formation 307 (FIG. 15) below the recess opening 350 in the housing halves 16a, 16b so that the linear control member 302 does not detach from the control handle 16. The longitudinal dimensions of the recess 350 and 307 which are both greater than the length of the linear control member 302 allow the control member and the control handle to slidably engage each other thus allowing distal and proximal linear movement of the control member along the longitudinal axis, as actuated by user to advance or retract the third puller member.

The body 307 of the cam 306 on which the rotational member 304 is supported also has a helical track 332 formed in an outer surface of the body 307. The track 332 extends between the collar 309 and a proximal end of the body. Riding in the track 332 is a finger 341 of a follower 340 generally situated between the cam 306 and the inner rotational member 304, whose movement is guided by an axial slot 342 formed in the rotational member 304 as the rotational member is rotated by the linear control member 302 by means of the projection 303 received in the helical track 305. A distal end of the contraction wire 35 is anchored to the finger 341 so that the follower 340 can move the contraction wire 35 longitudinally relative to the catheter body 12.

As a user moves the control member 302 linearly along the longitudinal axis 310, the projection 303 rotates the rotational member 304 by means of the track 305 thereon. As the rotational member 304 and its axial slot 342 rotate, so does the follower 340 within the slot 342, with all three orbiting the longitudinal axis of the cam and the control handle 16. As the follower 340 orbits, it finger 341 slides in the helical track 332 to move distally or proximally relative to the control handle 16. As the follower 340 slides distally, the contraction wire 35 is pushed distally to expand the mapping assembly 17. As the follower 340 slides proximally, the contraction wire is drawn proximally to contract the mapping assembly 17. Such is a means by which linear movement of the control member 302 is converted to a rotational movement by which the contraction puller member 35 is advanced or retracted within the control handle. Advantageously, the distance the follower 340 can travel along the helical track 332 is not limited to and in fact can be much greater than the length of the cylindrical body 307, for greater range or degree of motion in the catheter component controlled by the contraction wire 35. Indeed, the distance the follower 340 can travel (and hence amount by which the contraction wire 35 can be moved) along the cylindrical body 307 depends on the pitch of the helical track 332 (e.g., width of one complete helix turn) and the diameter of the cylindrical body 207.

The collar 309 of the cam 306 has a radial notch 344 through which the contraction wire 35 passes to reach the body 307. A lip 349 is formed at the proximal end of the body 307 of the cam 306 as a snap-fit feature to retain the rotational member 304 on the body 307. Axial notches 346 allow deformation or deflection of the proximal end of the cam 307 to facilitate the snap-fit feature. Lead wires and other components (e.g., thermocouple wires, cables, irrigation tubing) extending through the protective tubing 152 can pass through passage 348 of the cam.

Figure 32:
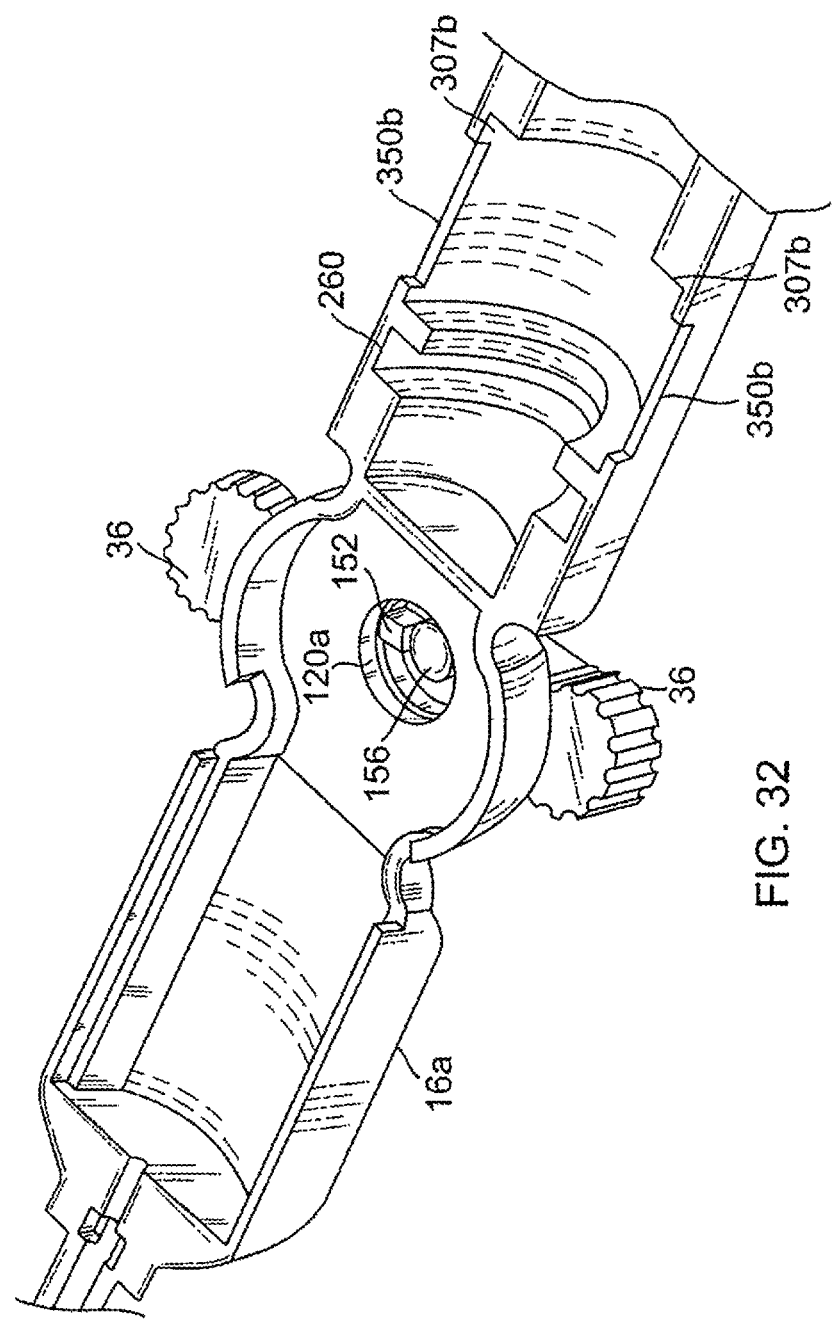
FIG. 32 is a partial perspective view of an alternate embodiment of a control handle housing half.

In an alternate embodiment, the linear control assembly includes a second linear control member 302b that diametrically opposes a first linear control member 302a on the control handle 16, as illustrated in FIGS. 28-31. Each linear control member has a projection 303a, 303b that engages a respective one of double helical tracks 305a and 305b provided on the inner rotational member 304. As illustrated in FIG. 32, the linear control members 302a, 302b slidably engage the control handle housing halves by means of opposing cutout formations 307a, 307b, respectively, and the projections 303a, 303b reaches the inner rotational member 304 through recess openings 350a, 350b, respectively. Thus, the user can use either linear control member to expand or contract the mapping assembly, where both linear control members move similarly and contemporaneously in response to actuation of either linear control member by the user.

In either of the foregoing embodiments, as a user pushes or pulls on a linear control member, the projection on the linear control member moves distally or proximally in a linear fashion which slides in a helical track on the rotational member to rotate the rotational member. As the rotational member rotates about the cam, its axial slot guides the follower to orbit about the cam. The follower slides in the cam track moving distally or proximally relative to the control handle. As the follower slides distally, the contraction wire is pushed distally, for example, to expand the mapping assembly. As the follower slides proximally, the contraction wire is drawn proximally, for example, to contract the mapping assembly.

It is understood that relative sizing of the components of the control assembly is not limited to the illustrated embodiments. Advantageously, the control assembly utilizes minimal space in the control handle for maximizing contraction and expansion of the mapping assembly by converting linear motion of the control member into rotational motion of the inner member which retracts and advances (or releases) the contraction wire in a linear fashion. For either embodiment, a suitable length L of the cam track about the cam can be $L=Pi*(D_E-D_C)$ where $D_E$ is the expanded diameter of the generally circular main portion 39 of the mapping assembly 17 and $D_C$ is the contracted diameter of the generally circular main portion 39.

In use, a suitable guiding sheath is inserted into the patient with its distal end positioned at a desired mapping location. An example of a suitable guiding sheath for use in connection with the present invention is the Preface™ Braiding Guiding Sheath, commercially available from Biosense Webster, Inc. (Diamond Bar, Calif.). The distal end of the sheath is guided into one of the chamber, for example, the atria. A catheter in accordance with the present invention is fed through the guiding sheath until its distal end extends out of the distal end of the guiding sheath. As the catheter is fed through the guiding sheath, the mapping assembly 17 is straightened to fit through the sheath. Once the distal end of the catheter is positioned at the desired mapping location, the guiding sheath is pulled proximally, allowing the deflectable intermediate section 14 and mapping assembly 17 to extend outside the sheath, and the mapping assembly 17 returns to its original shape due to the shape-memory of the support member 54.

By manipulating and rotating the deflection arm 75 of the deflection control assembly 74 to deflect the intermediate section 14, the mapping assembly 17 is then inserted into a pulmonary vein or other tubular region (such as the superior vena cava, or inferior vena cava) so that the outer circumference of the generally circular main region 39 of the assembly 17 is in contact with a circumference inside the tubular region. Turning the deflection arm 75 in one direction deflects the intermediate section 14 to that direction. Turning the deflection 75 in the opposite direction deflects the intermediate section 14 to that opposite direction. Tension of the deflection 75 is adjusted by manipulating and rotating the dial 101. Turning the dial 101 in one direction increases the tension. Turning the dial 101 in the opposition direction decreases the tension. Preferably at least about 50%, more preferably at least about 70%, and still more preferably at least about 80% of the circumference of the generally circular main region is in contact with a circumference inside the tubular region.

The circular arrangement of the electrodes 26 permits measurement of the electrical activity at that circumference of the tubular structure so that ectopic beats between the electrodes can be identified. The size of the generally circular main region 39 permits measurement of electrical activity along a diameter of a pulmonary vein or other tubular structure of or near the heart because the circular main region has a diameter generally corresponding to that of a pulmonary vein or other tubular structure. By manipulating the linear control member of the control assembly, the assembly 17, in particular, the generally circular main region 39, is adjusted to fit the pulmonary vein or other tubular structure. By pulling back on a linear control member, the contraction wire is drawn proximally to tighten and decrease the diameter of the generally circular region 39. By pushing forward on a linear control member, the contraction wire is pushed distally to release the generally circular region 39 and expands its diameter.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. For example, the catheter can be adapted such that the third puller member advances and retracts another component such as a guide wire or a needle. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:
1. A catheter comprising:
a catheter body;
a deflectable intermediate section distal the catheter body;
a mapping assembly distal the intermediate section, the mapping assembly having a generally circular portion;
a control handle proximal the catheter body, the control handle having a longitudinal axis and comprising:
a deflection control assembly comprising a deflection arm and a rocker member; and
a linear control assembly having a first control member, a second control member, an inner rotational member and a cam, the first and second control members configured for linear movement along the longitudinal axis of the control handle;

first and second puller members anchored to the deflection control assembly adapted to deflect the intermediate section; and a third puller member anchored to the linear control assembly configured to contract the generally circular portion of the mapping assembly, the third puller member extending along a longitudinal axis of the control handle and through a channel in the rocker member of the deflection control assembly.

2. The catheter according to claim 1, wherein the control handle further comprises a protective tubing through which the third puller member extends, the protective tubing extending along the longitudinal axis of the control handle and through the channel in the rocker member of the deflection control assembly.

3. The catheter according to claim 1, wherein the channel through the rocker member of the deflection control assembly extends through a width dimension of the rocker member of the deflection control assembly.

4. The catheter according to claim 1, wherein distal and/or proximal portions of the channel through the rocker member of the deflection control assembly comprise indents.

5. The catheter according to claim 4, wherein the indents in the channel are triangular-shaped indents or wedge-shaped indents.

6. The catheter according to claim 4, wherein the indents define a range of angles over which the rocker member can rotate, the range of angles being about ±45 degrees of the longitudinal axis of the control handle.

7. The catheter according to claim 1, wherein the rocker member of the deflection control assembly comprises first and second slots and first and second pulleys, wherein the first puller member enters the rocker member of the deflection control assembly through the first slot and is wound around the first pulley, and the second puller member enters the rocker member of the deflection control assembly through the second slot and is wound around the second pulley.

8. The catheter according to claim 7, wherein the first and second pulleys and the rocker member of the deflection control assembly are arranged such that rotation of the rocker member of the deflection control assembly in a first direction draws back one of the first and second puller members to thereby deflect the deflectable intermediate section.

9. The catheter according to claim 7, wherein each of the first and second puller members comprises a distal puller wire and a proximal tensile fiber, the distal puller wire and the proximal tensile fiber being connected within the control handle at a location distal the rocker member of the deflection control assembly.

10. The catheter according to claim 9, wherein the proximal tensile fiber is more flexible than the distal puller wire.

11. The catheter according to claim 9, wherein each of the proximal tensile fibers of the first and second puller members is wound around its respective first or second pulley and turns about 180 degrees to double back towards a distal end of the control handle.

12. The catheter according to claim 9, wherein each of the proximal tensile fibers of the first and second puller members is anchored by an anchor assembly comprising a pair of racks, a slug and a stop.

13. The catheter according claim 12, wherein a proximal end of each of the proximal tensile fibers extends within a channel defined by the respective pair of racks, and the proximal end of each of the proximal tensile fibers is encased within the respective slug which is sized to fit in and translate within the respective channel.

14. A multifunctional catheter control handle for use in a patient's heart, comprising:
a housing;
a deflection control assembly having a deflection arm and a rocker member;
a linear control assembly having a first linear control member, a second linear control member, an inner rotational member and a cam, the inner rotational member being rotatably mounted on the cam, the first and second linear control members configured for linear movement along the longitudinal axis of the control handle;
a tension adjustment assembly mounted on the housing configured to adjust tension of the deflection arm of the deflection control assembly;
at least a first puller member with a proximal end anchored to the deflection control assembly; and
an additional puller member with a proximal end anchored to the linear control assembly.

15. The multifunctional catheter control handle according to claim 14, wherein the tension adjustment assembly comprises:
a tension adjustment dial;
a locking plate;
a retaining nut; and
a washer,
wherein rotation of the tension adjustment dial in a first direction compresses the rocker member of the deflection control assembly against the washer, and rotation of the tension adjustment dial in a second direction opposite the first direction releases the rocker member from the washer.

16. The multifunctional catheter control handle according to claim 15, wherein the locking plate comprises one or more holes through which one or more prongs on the tension adjustment dial extend, and wherein the one or more prongs on the tension adjustment dial extend through the one or more holes of the locking plate and are received in one or more grooves in an outer surface of the housing.

17. The multifunctional catheter control handle according to claim 16, wherein the one or more grooves in the outer surface of the housing are configured to limit rotation of the tension adjustment dial in the first and second directions.

18. The multifunctional catheter control handle according to claim 15, wherein the locking plate is affixed to the tension adjustment dial, and the locking plate comprises one or more prongs received in one or more grooves in an outer surface of the housing.

19. The multifunctional control handle according to claim 18, wherein the one or more grooves in the outer surface of the housing are configured to limit rotation of the tension adjustment dial in the first and second directions.

20. A catheter comprising:
a catheter body;
a deflectable intermediate section distal the catheter body;
a mapping assembly distal the intermediate section, the mapping assembly having a generally circular portion and comprising a nonconductive tubing and a reinforcing ring mounted within a distal end of the nonconductive tubing, the reinforcing ring configured to maintain a diameter of the nonconductive tubing at its distal end;

a control handle proximal the catheter body, the control handle having a longitudinal axis and comprising:
  a deflection control assembly; and
  a linear control assembly having a first control member, a second control member, an inner rotational member and a cam, the first and second control members configured for linear movement along the longitudinal axis of the control handle;
first and second puller members anchored to the deflection control assembly adapted to deflect the intermediate section; and
a third puller member anchored to the linear control assembly configured to contract the generally circular portion of the mapping assembly.

* * * * *